US012670658B2

(12) United States Patent (10) Patent No.: US 12,670,658 B2
Fenster et al. (45) Date of Patent: Jun. 30, 2026

(54) SYSTEM AND METHOD FOR DISPLAY PLANE VISUALIZATION THROUGH AN ULTRASOUND IMAGING VOLUME

(71) Applicant: Aaron Fenster, London (CA)

(72) Inventors: Aaron Fenster, London (CA); Jeffrey Bax, Lucan (CA); David Tessier, London (CA); Igor Gyacskov, London (CA); Claire Keun Sun Park, Edmonton (CA); Tiana Trumpour, London (CA)

(73) Assignee: Aaron Fenster, London (CA)

( * ) Notice: Subject to any disclaimer, the term of this patent is extended or adjusted under 35 U.S.C. 154(b) by 24 days.

(21) Appl. No.: 18/438,704

(22) Filed: Feb. 12, 2024

(65) Prior Publication Data

US 2024/0282047 A1    Aug. 22, 2024

Related U.S. Application Data

(60) Provisional application No. 63/447,512, filed on Feb. 22, 2023.

(51) Int. Cl.
*G06T 15/08* (2011.01)
*A61B 8/00* (2006.01)
(Continued)

(52) U.S. Cl.
CPC ............ *G06T 15/08* (2013.01); *A61B 8/0825* (2013.01); *A61B 8/145* (2013.01); *A61B 8/4209* (2013.01);
(Continued)

(58) Field of Classification Search
CPC . G06T 15/08; G06T 2200/04; G06T 2200/24; G06T 2210/41; A61B 8/145;
(Continued)

(56) References Cited

U.S. PATENT DOCUMENTS 10,251,621 B2    4/2019  Zhang et al.
2003/0007598 A1 *  1/2003  Wang .................... A61B 6/463
                                                    378/37
(Continued)

FOREIGN PATENT DOCUMENTS

WO    WO-2019048284 A1 *  3/2019

OTHER PUBLICATIONS

Baltzer Pat, "Supplemental screening using breast MRI in women with mammographically dense breasts," Eur. J. Radiol., vol. 109513, No. 136, pp. 1-4, 2021, doi: 10.1016/j.ejrad.2020.109513.
(Continued)

*Primary Examiner* — Andrew W Begeman
(74) *Attorney, Agent, or Firm* — Brunet & Co. Ltd.; Robert Brunet; Hans Koenig

(57) ABSTRACT

A method and system for capturing and processing high-resolution three-dimensional medical images for oblique plane ultrasound generation and visualization through an ultrasound volume. Combining two three dimensional ultrasound datasets taken at different angles, each comprising a plurality of 2D ultrasound image planes, into a single combined dataset enables visualization of the ultrasound data at an oblique display plane through the volume being imaged in a standard computing system with an image processor.

20 Claims, 13 Drawing Sheets

(51) Int. Cl.
*A61B 8/08*          (2006.01)
*A61B 8/14*          (2006.01)

(52) U.S. Cl.
CPC .......... *A61B 8/4461* (2013.01); *A61B 8/4488*
(2013.01); *A61B 8/466* (2013.01); *A61B 8/483*
(2013.01); *G06T 2200/04* (2013.01); *G06T*
*2200/24* (2013.01); *G06T 2210/41* (2013.01)

(58) Field of Classification Search
CPC ..... A61B 8/4461; A61B 8/4488; A61B 8/466;
A61B 8/483
See application file for complete search history.

(56)                References Cited

U.S. PATENT DOCUMENTS

| | | | | |
|---|---|---|---|---|
| 2003/0216645 A1* | 11/2003 | Yao | ...................... | G01S 15/8993 |
| | | | | 600/437 |
| 2004/0087851 A1* | 5/2004 | Lee | ...................... | A61B 8/4209 |
| | | | | 600/407 |
| 2009/0003665 A1* | 1/2009 | Berg | ........................ | A61B 8/00 |
| | | | | 382/128 |
| 2012/0123267 A1* | 5/2012 | Dow | ...................... | A61B 8/483 |
| | | | | 600/443 |
| 2015/0018685 A1* | 1/2015 | Barker | ................. | A61B 8/4218 |
| | | | | 600/459 |
| 2015/0293215 A1* | 10/2015 | Kim | ................... | G01S 7/52047 |
| | | | | 367/7 |
| 2019/0336110 A1* | 11/2019 | Kustra | ................. | A61B 8/5253 |
| 2021/0275146 A1* | 9/2021 | Schlenger | ............ | A61B 8/4263 |
| 2022/0061803 A1* | 3/2022 | Venkataramani | .... | A61B 8/4263 |
| 2023/0346345 A1 | 11/2023 | Fenster et al. | | |

OTHER PUBLICATIONS

Fenster A, et al., "Three-dimensional ultrasound imaging," Phys. Med. Biol., vol. 46, No. 5, pp. R67-99, 2001, doi: 10.1088/0031-9155/46/5/201.

Guo, R, et al., "Ultrasound Imaging Technologies for Breast Cancer Detection and Management: A Review," Ultrasound Med. Biol., vol. 44, No. 1, pp. 37-70, 2018, doi: 10.1016/j.ultrasmedbio.2017.09.012.

Li T, et al., "Differential detection by breast density for digital breast tomosynthesis versus digital mammography population screening: a systematic review and metaanalysis," Br. J. Cancer, vol. 127, No. 1, pp. 116-125, 2022, doi: 10.1038/s41416-022-01790-x.

Nazari SS, et al., "An overview of mammographic density and its association with breast cancer," Breast Cancer, vol. 25, No. 3, pp. 259-267, 2018, doi: 10.1007/s12282-018-0857-5.

Park CKS, et al., "Spatially tracked whole-breast three-dimensional ultrasound system toward point-of-care breast cancer screening in high-risk women with dense breasts," Med. Phys., vol. 49, No. 6, pp. 3944-3962, 2022, doi: 10.1002/mp.15632.

Park C, et al., "Dedicated point-of-care whole-breast 3D ultrasound device." Presentation summary for AAPM 64th Annual Meeting & Exhibition. Jul. 12, 2022.

Park CK, et al., "Toward point-of-care breast cancer diagnosis: validation of a spatially tracked automated 3D ultrasound system," Proceedings of SPIE, vol. 1203804, No. April, p. 7, 2022, doi: 10.1117/12.2607552.

Smith WL, et al., "Optimum scan spacing for three-dimensional ultrasound by speckle statistics," Ultrasound Med. Biol., vol. 26, No. 4, pp. 551-562, 2000, doi: 10.1016/S0301-5629(99)00162-3.

Sprague BL, et al., "Prevalence of mammographically dense breasts in the United States," J. Natl. Cancer Inst., vol. 106, No. 10, pp. 1-6, 2014, doi: 10.1093/jnci/dju255.

Thouvenot A, et al., "Characterization of various tissue mimicking materials for medical ultrasound imaging," No. Apr. 2016, p. 97835E, 2016, doi: 10.1117/12.2218160.

Wang X, et al., "Elevation direction deconvolution in three-dimensional ultrasound imaging," IEEE Trans. Med. Imaging, vol. 15, No. 3, pp. 389-394, 1996, doi: 10.1109/42.500148.

* cited by examiner

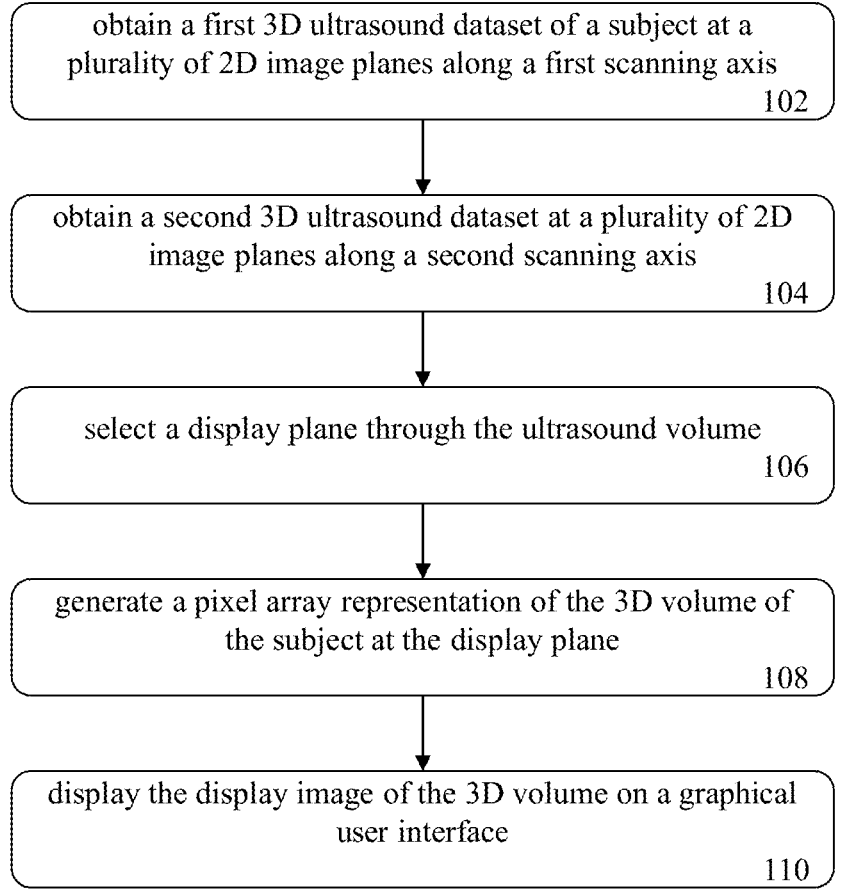

obtain a first 3D ultrasound dataset of a subject at a
plurality of 2D image planes along a first scanning axis
                                                    102 obtain a second 3D ultrasound dataset at a plurality of 2D
image planes along a second scanning axis
                                                    104 select a display plane through the ultrasound volume
                                                    106 generate a pixel array representation of the 3D volume of
the subject at the display plane
                                                    108 display the display image of the 3D volume on a graphical
user interface
                                                    110

Figure 3

SYSTEM AND METHOD FOR DISPLAY PLANE VISUALIZATION THROUGH AN ULTRASOUND IMAGING VOLUME

CROSS-REFERENCE TO RELATED APPLICATION

This application claims the benefit of United States Provisional patent application U.S. Ser. No. 63/447,512 filed Feb. 22, 2023, the entire contents of which are herein incorporated by reference.

FIELD OF THE INVENTION

The present invention pertains to a method and system for capturing and processing ultrasound images for generation of high-resolution images on a display plane through an ultrasound volume. The present system and method can be used to generate high resolution images in ultrasound imaging volumes for display planes that are out-of-plane or non-orthogonal to the acquired 2D ultrasound images.

BACKGROUND

Ultrasound (US) imaging is a widely available, cost-effective, and non-ionizing modality with unparalleled importance in clinical practice worldwide, enabling accessible and point-of-care applications, even in resource-limited settings. In particular in the monitoring and diagnosis of breast cancer, mammographic screening methods have improved treatment outcomes and reduced mortality through the early detection of breast cancer. However, the diagnostic sensitivity for detecting small, early-stage breast cancer is significantly reduced in patients with dense (small) breasts. When used for supplemental screening in asymptomatic intermediate to high-risk patients, including those with dense breasts, handheld ultrasound allows for the early detection of small, early-stage, and mammographically occult breast cancers.

In a clinical ultrasound imaging, 2D ultrasound (2DUS) images are generally acquired by a handheld device by an ultrasound technician at a variety of angles and then the captured 2D ultrasound images are read by a radiologist. Despite its clear evidence supporting early detection of breast cancers, handheld ultrasound still has several limitations, such as it is highly operator dependent, time consuming, and lacks reproducibility, which are important for reliably monitoring temporal changes of normal breast tissues and suspicious lesions. Moreover, handheld ultrasound is inherently 2D and has a small field-of-view, does not have volumetric capabilities, and also does not permit view planes parallel to the skin or chest wall. This limits the capability of ultrasound to provide a global display of the entire breast and surrounding anatomical structures in three-dimensions precluding its use for whole breast assessment. The complex dynamic between risk factors such as age, body mass index (BMI), breast density, reproductive factors, hormonal status, menopausal status, and increased mammographic density over time may further increase the uncertainty of breast cancer detection at the time of imaging. These variable uncertainties may also increase the number of false-positive findings, resulting in unnecessary breast biopsy procedures and interventions. Additionally, under current mammographic screening recommendations, the associated exposure due to ionizing radiation may not be ideal for screening, in particular, younger and high-risk patients with dense breasts.

Automated breast ultrasound (ABUS) overcomes many challenges associated with conventional handheld ultrasound imaging and can be used to acquire a plurality of 2D ultrasound images in a short period of time which can be reconstructed as a 3D ultrasound (3D US) image that can be reviewed with multiplanar 3D viewing software for whole breast assessment. ABUS systems have allowed for standardized acquisition, removing operator dependence, and improving reproducibility. However, high-quality 3D ABUS images are still reliant on operator training to ensure proper patient positioning and coupling to mitigate acquisition artifacts and commercially available 3D ABUS systems are relatively expensive as well as non-portable, as they require a complete system and workstation to be installed for use, which often includes an entire US machine that is designed to be compatible with specialized US transducers. As such, modern ABUS systems lack point-of-care (POC) capabilities which limits their bedside screening and diagnostic applications and limits access for patients.

Compared with specialized 3D ABUS systems, alternative, hybrid-type 3D ABUS systems integrate commercially available linear array or curvilinear ultrasound transducers with a computer-driven mechanism to generate a 3DUS image. While hybrid-type ABUS systems are generally more cost-effective, the intrinsic characteristics of conventional ultrasound transducers, such as linear array handheld ultrasound transducers, limit the resolution of the 3D ABUS images in the out-of-plane or scanning direction. In addition, while reconstructed 3DUS images from both 3D ABUS and hybrid-type 3D ABUS systems have high in-plane resolution, the out-of-plane resolution can be poor due to the elevational resolution component in the scanning direction unless high computing power machines are used for 3D volumetric reconstruction of the acquired images. Specifically, at any 2D view plane slice of the 3D ultrasound image that is oblique to the scanning plane, the resolution observed will include components from the high in-plane resolution and poor out-of-plane resolution, which will diminish the overall resolution, resulting in blurred structures.

Some studies have been conducted to improve out-of-plane resolution in 3DUS images. Analogous to 2DUS cases, multi-modal image registration and reconstruction are of interest for improving spatial resolution. With this technique, a small region-of-interest (ROI) is imaged with 3DUS and a secondary 3D imaging modality. The 3DUS image is sub-sampled to extract the course, visible data from the ultrasound image, while the fine samples in shadowed regions are interpolated from the alternate modality. Sub-sampling interpolation has also been applied to freehand 3DUS imaging, removing the need of a secondary modality. Speckle decorrelation techniques have also been leveraged to sub-sample the out-of-plane resolution and perform reconstruction for enhancement. While the aforementioned approaches can improve out-of-plane resolution, these techniques require complex computational approaches. Moreover, acquisition approaches and techniques to improve isotropic 3D resolution across all dimensions (axial, lateral, and elevational directions) are not readily available.

With increasing evidence for ABUS for screening breast cancer, there is an interest in developing more robust, cost-effective, and high-resolution techniques to improve breast imaging for the detection and characterization of breast lesions. In one example, U.S. Pat. No. 10,251,621B2 to Zhang et al. describes a method and system for acquiring, processing and displaying breast ultrasound images that excludes obscuring influences of non-breast structures to reduces the occurrence of missing cancers in screening and diagnosis.

Improving accessible, cost-effective methods for the early detection of breast cancer remains a challenge in develop- ment and clinical practice, particularly in the intermediate to high-risk population of women with dense breasts and in non-urban populations. With increasing evidence for the effectiveness and convenience of three-dimensional (3D) automated breast ultrasound systems (ABUS) for screening breast cancer in intermediate to high-risk patients, there is increasing need for developing robust, cost-effective, and high-resolution ultrasound imaging techniques for bedside point-of-care imaging and for improved screening methods. There also remains an unmet need to improve ultrasound image resolution, specifically in the out-of-plane (eleva- tional) scanning direction, and to improve the resolution for ultrasound data visualization at oblique angles relative to the ultrasound image acquisition planes.

This background information is provided for the purpose of making known information believed by the applicant to be of possible relevance to the present invention. No admis- sion is necessarily intended, nor should be construed, that any of the preceding information constitutes prior art against the present invention.

SUMMARY OF THE INVENTION

An object of the present invention is to provide a method and system for capturing and processing high-resolution images for oblique plane ultrasound image generation and visualization through an ultrasound volume. Another object of the present inventions is to provide a system and method that can be used to generate high resolution images in 3D ultrasound and other imaging for visualization of viewing planes that are out-of-plane or non-orthogonal to a set of acquired 2D planar images.

In an aspect there is provided a computer-implemented imaging method comprising: acquiring a first plurality of two dimensional (2D) ultrasound images through an ultra- sound volume, the first plurality of 2D ultrasound images normal to a first scanning axis, to provide a first three dimensional ultrasound (3DUS) dataset; acquiring a second plurality of 2D ultrasound images through the ultrasound volume, the second plurality of 2D ultrasound images nor- mal to a second scanning axis, the second scanning axis at an offset angle to the first scanning axis, to provide a second 3DUS dataset; selecting a display plane at a display angle to the first scanning axis and the second scanning axis through the ultrasound volume; constructing a display image at the display plane by calculating pixel intensity for the plurality of pixels in the image at the display plane using pixel weighting based on the display angle relative to the first scanning axis and the second scanning axis; and displaying the display image at the display plane on a graphical user interface.

In an embodiment, each of the 2D ultrasound images are acquired at a consistent step interval.

In another embodiment, the step interval is a spatial interval or a temporal interval.

In another embodiment, each acquired 2D ultrasound image has a volumetric plane width greater than the step interval.

In another embodiment, the step interval is from 1 to 10 frames per mm.

In another embodiment, constructing the display image at the display plane comprises using the same pixel weighting algorithm for calculating pixel intensity for all of the plu- rality of pixels in the image at the display plane.

In another embodiment, the offset angle is 90°.

In another embodiment, the ultrasound transducer has a minimum penetration depth of 30 mm.

In another embodiment, pixel weighting for each of the plurality of pixels in the display image at the display plane comprises using a spherical-weighted algorithm.

In another embodiment the method further comprises normalizing pixel intensity values in the display plane by comparing pixel intensity at a coordinate location (x,y,z) in the first 3DUS and the second 3DUS and adjusting the pixel intensity in the display plane such that the pixel intensity for the first 3DUS dataset and the second 3DUS dataset are normalized.

In another embodiment, the first 3DUS dataset and the second 3DUS dataset are registered and fused using a rigid registration and voxel-based algorithm.

In another embodiment, the 2D ultrasound images contain intensity information from both in-plane and out-of-plane directions.

In another embodiment, the first plurality of 2D ultra- sound images and second plurality of 2D ultrasound images are acquired with one or more of a linear transducer, a curvilinear transducer, a phased-array transducer, or a trans- ducer that emits a single or multiple ultrasound wavelengths.

In another embodiment the method further comprises displaying a plurality of images at the same time, wherein each of the plurality of images is constructed at a different display plane through the ultrasound volume.

In another embodiment, each of the first scanning axis and the second scanning axis have a length of from 10 to 300 mm.

In another aspect there is provided an imaging system comprising: an ultrasound transducer; a 3D imaging device comprising a translation mechanism that positions and trans- lates the ultrasound transducer along a first scanning axis and a second scanning axis to collect a first 3DUS dataset normal to the first scanning axis and a second 3DUS dataset normal to the second scanning axis; an imaging device control system that controls translation of the transducer; an image processor that constructs a display image on a display plane at a display angle through the first 3DUS dataset and the second 3DUS dataset using pixel weighting based on the display angle relative to the first scanning axis and the second scanning axis; and a graphical user interface for displaying the display image.

In an embodiment, the ultrasound transducer is a hand- held ultrasound transducer connected to the translation mechanism.

In another embodiment, the image processor registers the first 3DUS dataset and the second 3DUS dataset using a rigid registration and voxel-based algorithm.

In another embodiment, transducer location information is provided from the imaging device control system to the image processor and used in registering the first 3DUS dataset and the second 3DUS dataset.

In another embodiment, the ultrasound transducer is one of a linear transducer, a curvilinear transducer, a phased- array transducer, or a transducer that emits a single or multiple ultrasound wavelengths.

Embodiments of the present invention as recited herein may be combined in any combination or permutation.

BRIEF DESCRIPTION OF THE FIGURES

For a better understanding of the present invention, as well as other aspects and further features thereof, reference is made to the following description which is to be used in conjunction with the accompanying figures which illustrate embodiments or aspects of the invention, where:

FIG. 3 is a flowchart illustrating a method of obtaining an oblique display plane image in 3D ultrasound imaging;

DETAILED DESCRIPTION OF THE INVENTION

Figure 1:
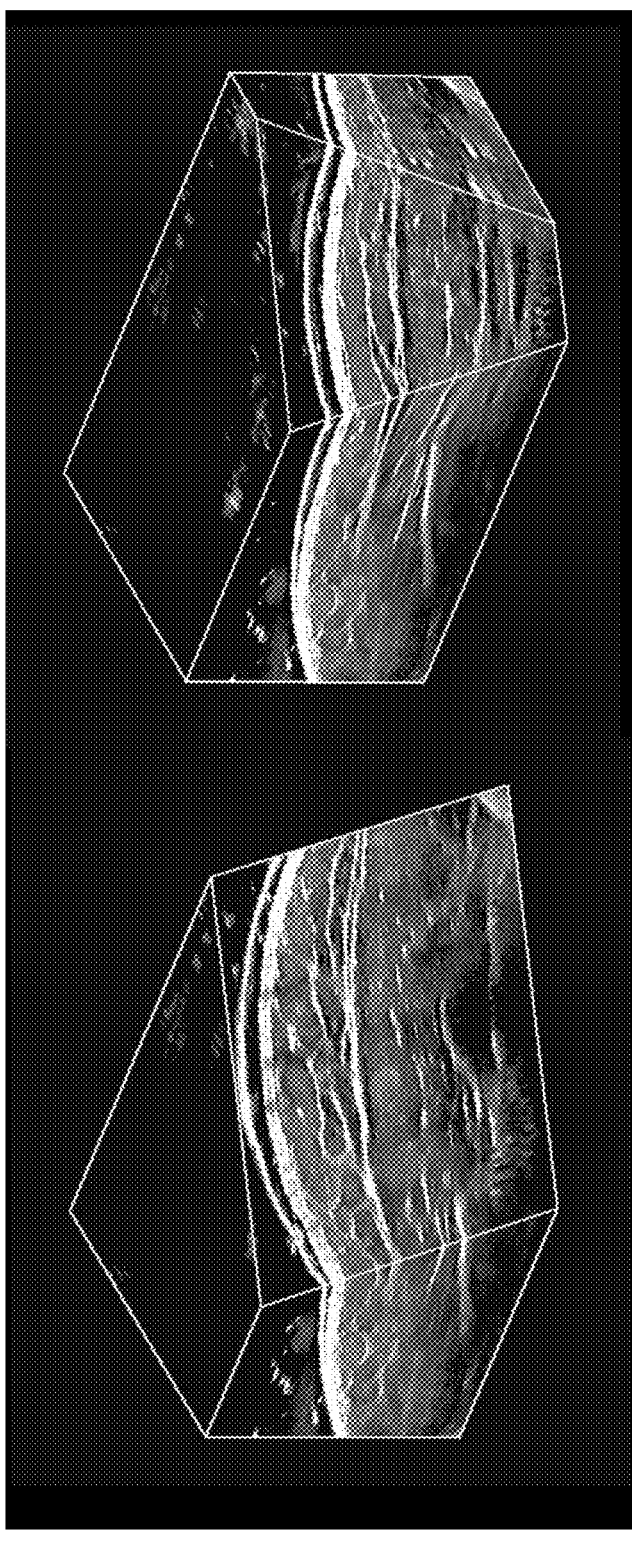
FIG. 1 is a 3D Automated breast ultrasound (ABUS) image with an oblique angle display plane and three orthogonal display planes.

Unless defined otherwise, all technical and scientific terms used herein have the same meaning as commonly understood by one of ordinary skill in the art to which this invention belongs. Working examples provided herein are considered to be non-limiting and merely for purposes of illustration.

As used in the specification and claims, the singular forms "a", "an" and "the" include plural references unless the context clearly dictates otherwise.

The term "comprise" and any of its derivatives (e.g. comprises, comprising) as used in this specification is to be taken to be inclusive of features to which it refers, and is not meant to exclude the presence of any additional features unless otherwise stated or implied. The term "comprising" as used herein will also be understood to mean that the list following is non-exhaustive and may or may not include any other additional suitable items, for example one or more further feature(s), component(s) and/or element(s) as appropriate.

As used herein, the terms "having", "including", and "containing", and grammatical variations thereof, are inclusive or open-ended and do not exclude additional, unrecited elements and/or method steps, and that that the list following is non-exhaustive and may or may not include any other additional suitable items, for example one or more further feature(s), component(s) and/or element(s) as appropriate. A composition, device, article, system, use, process, or method described herein as comprising certain elements and/or steps may also, in certain embodiments consist essentially of those elements and/or steps, and in other embodiments consist of those elements and/or steps and additional elements and/or steps, whether or not these embodiments are specifically referred to.

As used herein, the term "about" refers to an approximately +/−10% variation from a given value. It is to be understood that such a variation is always included in any given value provided herein, whether or not it is specifically referred to. The recitation of ranges herein is intended to convey both the ranges and individual values falling within the ranges, to the same place value as the numerals used to denote the range, unless otherwise indicated herein.

The use of any examples or exemplary language, e.g. "such as", "exemplary embodiment", "illustrative embodiment" and "for example" is intended to illustrate or denote aspects, embodiments, variations, elements or features relating to the invention and not intended to limit the scope of the invention.

As used herein, the terms "connect" and "connected" refer to any direct or indirect physical association between elements or features of the present disclosure. Accordingly, these terms may be understood to denote elements or features that are partly or completely contained within one another, attached, coupled, disposed on, joined together, in communication with, operatively associated with, etc., even if there are other elements or features intervening between the elements or features described as being connected.

As used herein, the term "3D ultrasound" and its acronym "3DUS" refers to a three dimensional dataset comprising a plurality of 2D ultrasound image planes taken of an ultrasound subject at a plurality of spaced apart locations, which together represent a three-dimensional view of the subject. In the present disclosure examples are provided where the ultrasound subject is a breast, however it is understood that similar or the same ultrasound methods can be used for other anatomical subjects, veterinary subjects, and also geological subjects.

Herein is described a system and method for acquisition and processing of volumetric ultrasound images for oblique plane and out-of-plane ultrasound generation and visualization through an ultrasound volume. The present system and method can be used to generate high resolution images in 3D ultrasound for non-oblique viewing planes and out-of-plane using a standard handheld ultrasound transducer together with a translation mechanism connected to the transducer. Using a standard handheld ultrasound transducer and a device or structure that connects to the transducer to capture a plurality of 2D ultrasound images along a normal to each of two scanning axes, two separate 3DUS volumetric datasets can be acquired. These datasets can be used to create a combined 3DUS (C3DUS) dataset for high resolution ultrasound image display. The presently described method and system transforms these two sets of two-dimensional ultrasound (2DUS) image planes into high resolution oblique plane images with inexpensive equipment to produce a high quality, high resolution plane cutting through the 2DUS image plane datasets that is viewable at any angle through the combined 3DUS image and suitable for diagnostic purposes.

The presently described method and system provides for a high resolution display plane image to be quickly generated from any clinically desired viewing angle using the two separate 3DUS volumetric datasets, using inexpensive equipment and reduced computing power as compared with conventional methods that employ a three-dimensional model. By acquiring two sets of two dimensional ultrasound (2DUS) image planes at an offset angle, the present method and system can transform two 3D ultrasound image sets into a combined 3DUS dataset that can be graphically viewed in 3D space in a graphical user interface at any display angle with limited processing requirements, displaying high resolution images in real time. In this way, a rapid and accurate method is provided to combine two sets of orthogonal or non-parallel 3D ultrasound (3DUS) image sets to improve resolution uniformity at any display plane in the combined 3D ultrasound image dataset of the ultrasound volume. As a result, multiplanar reconstruction and three-dimensional (3D) volumetric visualization can be provided in real time with inexpensive equipment and devices with limited computing power to enable point-of-care imaging and diagnostic visualization. By combining 3DUS images taken at an offset angle, resolution and uniformity of the subject imaging can be improved by recovering out-of-plane resolution in the scanning direction to provide higher resolution pixel representation in an oblique angle display plane and at planes in the subject volume that are out of plane from the 2D ultrasound images that make up the 3DUS datasets. Although it is preferable that the offset angle of the two 3DUS dataset is 900 and all examples provided herein illustrate an orthogonal offset angle, it is understood that the offset angle can be any known angle from 0-90° with post-processing of data from the acquired 2D image planes to mathematically and angularly normalize the 3DUS datasets to accommodate for the offset angle.

FIG. 1 is a 3D Automated breast ultrasound (ABUS) image with an oblique angle display plane and three orthogonal display planes showing two different oblique views of the 3DUS image of the breast of a healthy male volunteer. The image displayed at the display plane through the ABUS image can be positioned at any display angle through the ultrasound volume and thought of as any display plane that transects the ultrasound volume. In this way, any image through the ultrasound volume at any display angle can be visualized, for example at any angle between 0-90° of the acquired 2DUS image planes in any 3D cartesian direction. Accordingly, the display plane can be normal to any of the 2DUS image planes that make up the 3DUS datasets, or can be non-normal (or non-parallel), also referred to as 'oblique', to any of the 2D ultrasound acquisition planes that make up the 3DUS datasets. It is also evident that the display plane can also be non-normal to the scanning axis of ultrasound acquisition in both of the 3DUS images that make up the combined 3DUS image dataset. The further ultrasound travels the weaker the images become, which makes it more difficult to capture images of deeper parts of the body. By capturing two 3DUS image sets and combining them to create a single combined 3DUS dataset the present method and system results in greater resolution through the ultrasound volume.

Combined 3D ultrasound (C3DUS) as presently described improves resolution uniformity from both in-plane to out-of-plane acquisition directions during visualization of the ultrasound object at an angle oblique from the scanning axis in either of the 3DUS datasets that make up the CBUS dataset. Using 3DUS images where the scanning axis of a first 3DUS acquisition dataset is preferably perpendicular or orthogonal to the scanning axis of a second 3DUS acquisition dataset optimally provides volumetric data in the out-of-plane regions of the 2D image planes in each of the 3DUS datasets which can be accurately extrapolated using pixel averaging to provide high resolution display planes at oblique angles to the scanning axes and 2D image planes of the 3DUS datasets.

This combined 3DUS data acquisition and visualization is a versatile method to improve 3DUS image resolution with image acquisition using a mounting device in combination with any conventional linear or curvilinear array ultrasound transducer. The present combined 3DUS system and its proposed high-resolution complete 3D breast ultrasound screening approach can improve diagnostic implications for breast cancer screening for increased-risk populations and limited-resource settings. With the use of the present 3D ultrasound methods and an extended volumetric field-of-view, the sensitivity and specificity to detect breast lesions increases. Specifically, C3DUS enables high-resolution breast ultrasound image visualization at planes orthogonal obliquely angled relative to the planes on which the ultrasound was collected, providing robust, cost-effective, and computationally efficient imaging method for improving diagnostics for patients with small and/or dense breasts and increased-risk populations, and in limited-resource settings.

Figure 2:
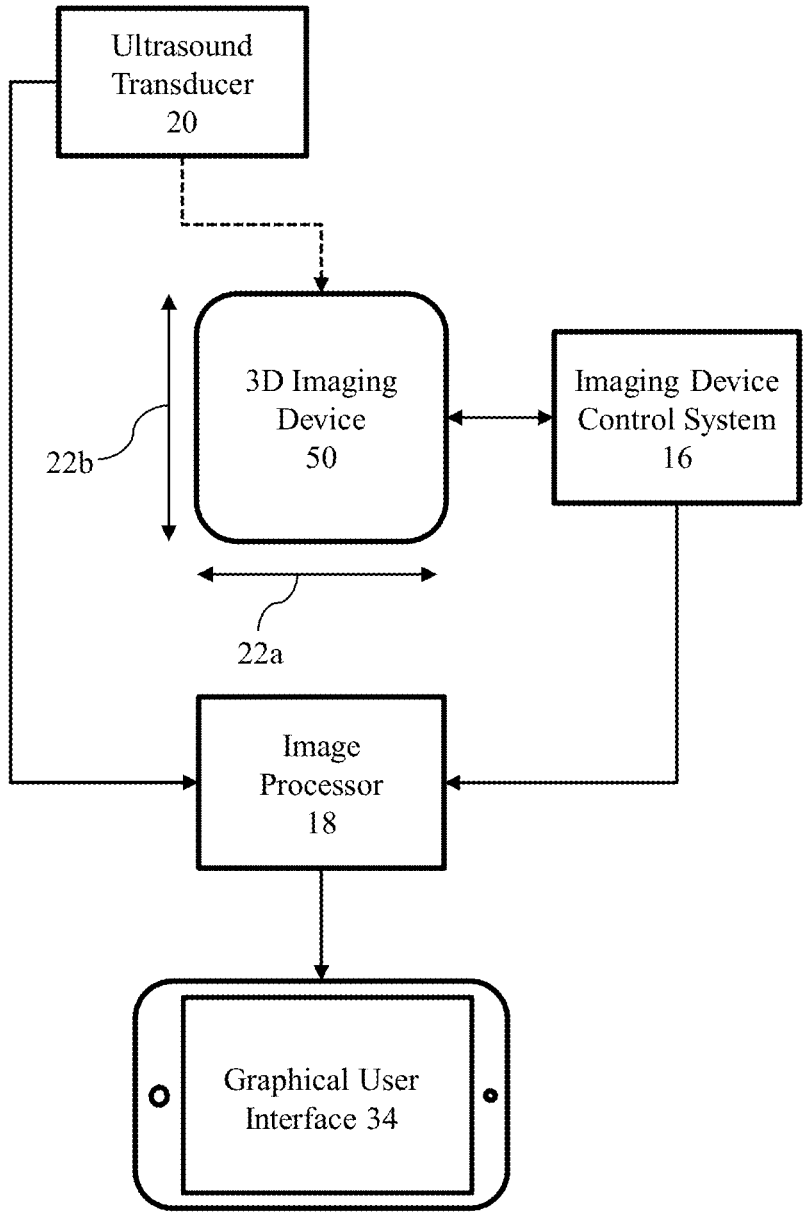
FIG. 2 illustrates a system for oblique plane visualization in 3D ultrasound imaging.

FIG. 2 illustrates a system for oblique plane visualization in 3D ultrasound imaging. The system comprises an ultrasound transducer 20 which is connected to a 3D imaging device 50 for obtaining multiple 2D ultrasound images along a scanning axis 22a, 22b. The imaging device 50 has a mechanism for securing and advancing the ultrasound transducer 20 along the scanning axis at regular known intervals, referred to herein as the step interval, to obtain a plurality of 2D images of the subject inside the volumetric space encapsulated by the 3D imaging device 50. Imaging device control system 16 controls the movement of the transducer along the scanning axis and relays transducer location information to the image processor to anchor the ultrasound data acquired by the transducer in 3D space. The 3D imaging device 50 can be a rectangular structure with a translation mechanism for connecting to the ultrasound transducer 20 to the device, or may be comprised of any other structure that can support and position an ultrasound transducer 20 at a plurality of incremental steps along each scanning axis 22a, 22b in order to obtain a plurality of 2D images at two different angles through an object volume to capture two different 3D ultrasound images. Once a 3DUS is obtained along the first scanning axis 22a and/or the second scanning axis 22b the datasets can be sent to the image processor 18 which is operatively connected to a graphical user interface 34. Preferably the image processor 18 and graphical user interface 34 are in the same electronic device, which can be, for example, a smartphone, tablet, laptop, or desktop computer. Because the combined 3DUS dataset can be easily accessed with limited computing power, a standard image graphics processor can be used to generate a high resolution image on a display plane at any clinically relevant viewing angle in the 3D volume of the ultrasound subject.

In cases where the scanning axes 22a, 22b are not orthogonal to one another the image processor 18 can also apply an angle normalization to locate or register each pixel in each of the 2D image sets on an (x,y,z) coordinate system in the same volumetric space. The combined 3DUS ultrasound dataset can then be made available by the image processor 18 to the graphical user interface 34 to enable a radiologist or trained professional to read the image at any angle for diagnostic purposes. Because oblique angle image construction from the combined 3DUS dataset can be easily done using the present method, visualization of a display image on an obliquely angled display plane can be done on the graphical user interface in real time. In addition, an image processor 18 of the type found on a mobile phone or tablet is sufficient to perform high resolution and rapid image processing such that diagnostic visualization can be accomplished locally at high speed and without a high powered dedicated processor. The system can also comprise or be connected to one or more data storage systems for storing the 3DUS datasets, which can be, for example, one or more of a memory device, memory card, hard disk drive, solid-state drive, cloud storage, or other data storage device.

The ultrasound transducer 20 can be any standard hand-held transducer, including but not limited to linear transducers, curvilinear transducers, phased-array transducers, and transducers that emit a single or multiple ultrasound wavelengths. One or more ultrasound frequencies can be used which can be combined and transmitted simultaneously to provide higher penetrating systems with higher resolution detail at more distal locations in the body from the scanning plane.

Although ultrasound is provided as an example imaging modality that can be used with the present system and method, it is noted that any 3D imaging modality for which data is collected in 2D planes at two scanning axes can employ the present method to extrapolate out-of-plane data to generate a display image at a display plane at any display angle in the data acquisition volume. Other imaging modalities that can utilize the present method include but are not limited to computer tomography scanning, X-ray scanning, magnetic resonance imaging scanning, positron emission tomography scanning, infrared scanning, and other sonography.

FIG. 3 is a flowchart illustrating a method of obtaining an oblique display plane image in 3D ultrasound imaging. First a 3D ultrasound dataset of a subject or 3D volume is obtained at a plurality of 2D image planes along a first scanning axis 102 to provide a first 3D ultrasound (3DUS) image along the first scanning axis. A second 3D ultrasound dataset of the same or partially overlapping 3D volume at a plurality of 2D image planes along a second scanning axis 104 to provide a second 3D ultrasound (3DUS) image along the second scanning axis. The two 3DUS datasets, each acquired at a different angle through the same 3D volume, can be used together and are referred to herein as a combined 3D ultrasound (C3DUS). To view any section through the 3D volume, the viewing or display plane can be selected by the use of a graphical user interface. In this way, a clinician can more easily view cross-sections through the 3D volume that may be suspicious as regions of interest in the 3D ultrasound image. In particular, the present method and system can be used to select an oblique display plane, or a display plane that is out of plane relative to the 2D image planes that make up each 3DUS image, through the 3D volume 106. The display image on the display plane at the oblique or out-of-plane angle can be generated by creating a pixel array representation of the 3D volume of the subject at the display plane 108 by applying a pixel-weighting algorithm such as a spherical-weighted algorithm, or any other algorithm that utilizes data from the 3DUS datasets based on the display angle relative to the first scanning axis and the second scanning axis. Finally, the display image of the 3D volume can be displayed on a graphical user interface 110.

Figures 4A, 4B:
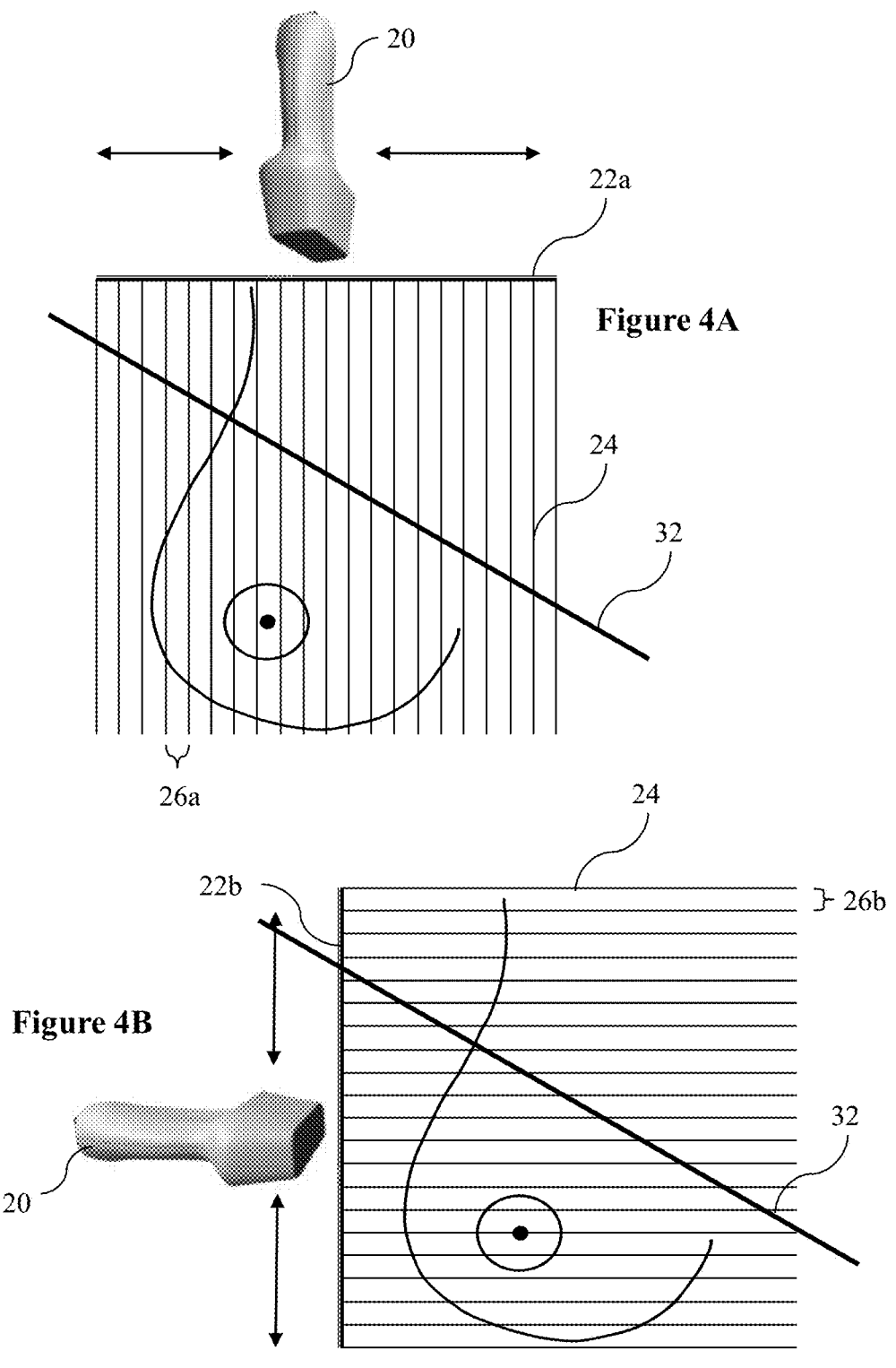
FIG. 4A is an illustration of a top view of acquisition of a plurality of 2D breast ultrasound images from a transducer sweep along a craniocaudal plane scanning axis.
FIG. 4B is an illustration of a top view of acquisition of a plurality of 2D breast ultrasound images from a transducer sweep along a mediolateral plane scanning axis.

FIG. 4A is an illustration of a top view of acquisition of a plurality of 2D breast ultrasound images from a transducer sweep along a craniocaudal plane scanning axis and FIG. 4B is an illustration of a top view of acquisition of a plurality of 2D breast ultrasound images from a transducer sweep along a mediolateral plane scanning axis. In FIG. 4A an ultrasound transducer 20 is translated along a craniocaudal scanning axis 22a at a consistent and known 2D plane step interval 26a to acquire a plurality of 2D ultrasound image planes 24 parallel in the mediolateral plane which make up a first 3DUS dataset. Similarly, in FIG. 4B, the ultrasound transducer 20 is translated along a mediolateral scanning axis 22b at a consistent and known 2D plane step interval 26b to acquire a plurality of 2D ultrasound image planes 24 parallel in the craniocaudal plane which makes up a second 3DUS dataset. Either one of these two 3DUS datasets can be thought of as a single ABUS dataset. The two 3DUS image sets are acquired at an offset angle, which is the angle between the first scanning axis 22a and the second scanning axis 22b, and can be utilized together to create a combined 3D ultrasound (C3DUS) dataset. In the case shown, the first scanning axis 22a is orthogonal to the second scanning axis 22b, however this is not required and pixel data in both sets of 3DUS image datasets can be normalized by the offset angle if the offset angle is less than 90°. Combining the two 3DUS datasets into a single C3DUS dataset enables visualization of the ultrasound data at oblique display plane 32 that is generated using data from a plurality of 2D ultrasound image planes in a standard computing system with an image processor.

Acquisition of each of the two 3D ABUS images in the illustrated method involves continually acquiring spatially encoded 2D ultrasound images at a selectable and consistent interval, referred to herein as the step interval, as the transducer is translated along the scanning axis. It is noted that the step interval can be a spatial interval or a temporal interval. While the reconstructed 3D ultrasound images have high in-plane (axial and lateral) resolution, the out-of-plane (elevational) resolution in the scanning direction is poor due to the in-plane focusing characteristics of conventional linear arrays and curvilinear ultrasound transducers. Therefore, at any view plane in the 3D ABUS image that is oblique to the in-plane acquisition direction, voxels in the 3D image include a combination of the high in-plane and poor out-of-plane resolution, which will diminish the overall 3D image resolution. This anisotropic resolution results in blurred structures and loss of anatomical details, which limits the quality of the 3D ABUS image. In contrast, through use of the present method and system, the two acquired 3D ABUS images can be combined for visualization and image analysis, wherein a real-time ultrasound display at the selected cross sectional plane through the volume can be generated with high resolution and with minimal processing power. In FIGS. 4A and 4B the ultrasound transducer is shown on scanning axes 22a, 22b positioned along two sides of a breast, however it is understood that in other embodiments the transducer can be positioned facing into the breast from the top, and two different 2DUS image datasets can be taken along two different directions from on top of the breast. It is noted that in prior art clinical ABUS systems, a single transducer sweep is generally used to take a single image set along a single scanning axis on top of the breast.

Figure 5:
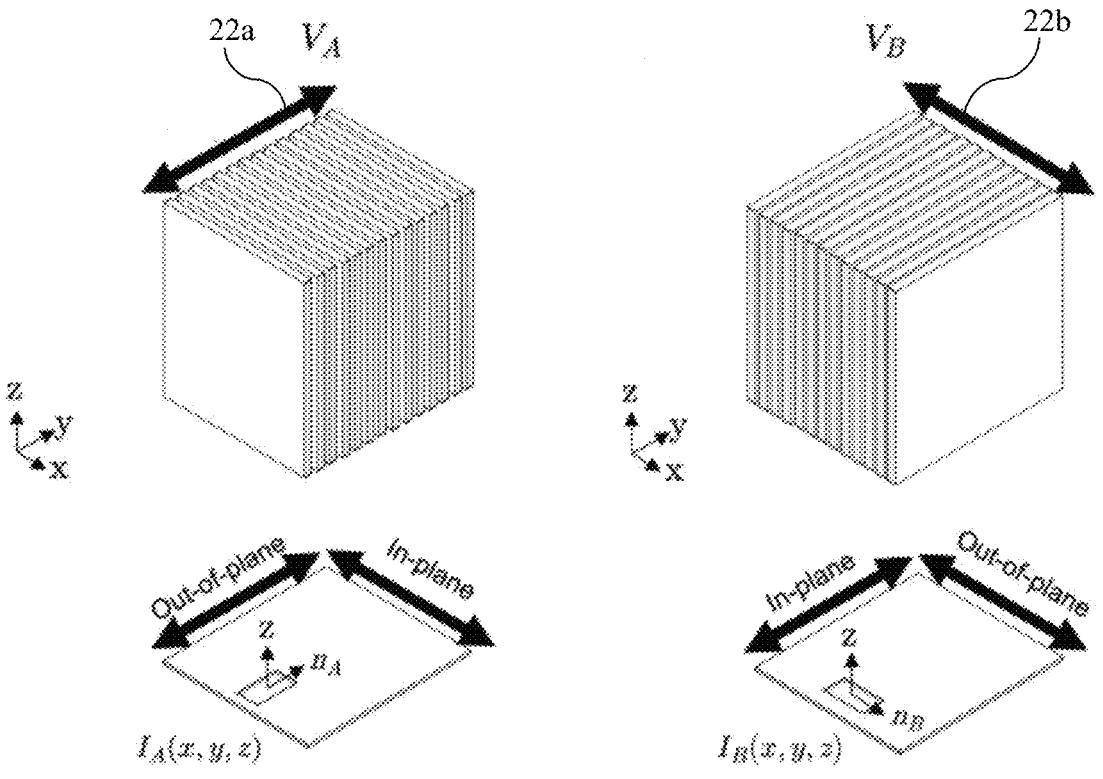
FIG. 5 is a volumetric representation of orthogonal 2D ultrasound image capture to acquire two 3DUS datasets at orthogonal scanning axes.

FIG. 5 is a volumetric representation of orthogonal 2D ultrasound image capture to acquire two 3DUS datasets at orthogonal scanning axes. In acquiring a 2D ultrasound image the ultrasound transducer emits waves in the ultrasound range and receives back an intensity of ultrasound waves at a bounceback frequency and in an intensity that is indicative of the tissue interfaces and tissue ultrasound scattering regions at any distance from the transducer. The intensity of the ultrasound bounceback signal as received by piezoelectric crystals in the ultrasound transducer can then be translated into pixel intensity at that location in the volume. To create a 3D image of an anatomy in accordance with the present method, two sets of 2D images are acquired along two scanning axes, first scanning axis 22a and second scanning axis 22b, which are angularly offset at an offset angle which is greater than 0° and no more than 90°. Stepwise advancement of the ultrasound transducer at a standard step interval along each of the two scanning axes provides a normalized protocol for 2D data acquisition such that the resulting 3D image has a normalized pixel set which is an averaged representation of the ultrasound measurement for each volume at each step interval.

Collection of the 2D image sets along each scanning axis is used for creating the 3D ultrasound (3DUS) image. To create a combined 3DUS (C3DUS) dataset of two image volumes, $V_A$ and $V_B$, the plurality of 2DUS image planes which make up each 3DUS image must be acquired at an offset angle around a shared axis. In the case shown the axes are orthogonal, meaning the acquired 2D ultrasound images planes for $V_A$ and $V_B$ are obtained at 90° to one another. This approach requires that the acquired 2D ultrasound images occupy the same volume and contain substantial overlap in physical space such that the captured 2D planes be anchored in space relative to one another to match pixels in each of the 2D ultrasound images to create the C3DUS image dataset. To acquire the first 2D image set, $V_A$, the ultrasound transducer is affixed to a stable translation assembly to scan in a first scan direction along a first scanning axis at a regular step interval. To acquire a second 2D image set, $V_B$, the ultrasound transducer is repositioned to scan in a scan direction along a second scanning axis. In breast imaging the first transducer axis can be, for example, along the mediolateral lateral plane, and the second transducer plane can be along the craniocaudal which is anatomically 90° or orthogonal. Using an ABUS scanning device that anchors the anatomy in space such that the first transducer plane is orthogonal to the second transducer plane ensures that the two sets of 2D ultrasound image planes captured are orthogonal to each other and can be normalized to provide the 3D ultrasound dataset.

With the two acquired orthogonal sets of 2D ultrasound images, a combined 3DUS dataset, also referred to as a complementary breast ultrasound (CBUS) image, can be generated. To create the CBUS image, two at least partially overlapping 3DUS datasets are registered and fused using a rigid registration and voxel-based algorithm. This can also be accomplished using common image features observed in both 3DUS datasets and registering the two 3DUS datasets by anchoring the common features. In another embodiment, data pertaining to the location of the ultrasound transducer in space, such as data used by the control system to translate the ultrasound transducer along the ultrasound volume, can be used to assign locational data to the acquired 2DUS images. Accordingly, the registration and fusing of the 3DUS datasets can comprise one or more of mechanical, electrical, or software methods, or a combination thereof. In one example method of registering the 3DUS datasets in space, the planar 2D ultrasound images are rigidly registered using their axis of rotation defined by the physical configuration of the scanner assembly, where the two scanning axes along which the 2D ultrasound image planes are captured are anchored at a normal to one other.

In each original 3D US image, the 3D voxels, which are represented by pixels in the 2D ultrasound image planes, contain intensity information from both in-plane (acquisition) and out-of-plane (scanning) directions, where the intensity value at any voxel is given by $I_A(x, y, z)$ and $I_B(x, y, z)$ for $V_A$ and $V_B$, respectively. In one example, to assign a signal intensity to any pixel location on any display plane through the volume in 3D space a pixel-weighting algorithm such as a spherical-weighted algorithm can be used to perform an intensity to calculate a signal intensity at any given pixel in the 3D image space. In addition, other methods to determine weighting factors may be used, preferably any function where weighting factors of contribution to the pixel intensity in the display plane adds up to 1, and then normalized to the sum of two values. In another method the pixel-weighting can use a nearest neighbor averaging method combined with the spatial relationship based on the angle of the display plane to the scanning axis of the 3DUS datasets. Preferably, every pixel in the display image at the display plane will use the same pixel-weighting algorithm, reducing processing requirements and enabling rapid image generation at one or more display planes.

In a spherical-weighted pixel-weighting, if the normal of the coronal xz-plane of $V_A$ is defined as coincident with the y-axis, then the normal to plane in $V_B$ is coincident with the x-axis, when acquired orthogonally. To recover the degradation of resolution due to poor out-of-plane resolution, any view plane obtained during multiplanar reformatting by slicing the 3D ultrasound image can be obtained from the spherical-weighted combination of the two pixels in corresponding planes that intersect at the (x,y,z) location in the 3D volume. The operation of extrapolating the 3D voxel intensity of all voxels on the display plane using the two intersecting 2D pixel intensities at their overlap coordinates (x,y,z) in 3D space can be performed in real-time. Alternatively, post-processing of data from the plurality of orthogonal 2D ultrasound image planes can generate the desired display plane of the 3D ultrasound image, which can then be rendered by an image processor. A spherical-weighted algorithm is used in this example to calculate signal intensity at any location (x, y, z) in the volumetric region, however it is understood that other pixel intensity averaging algorithms may be used.

Any 2D display plane in the 3D ultrasound image will be oriented at two angles: $\phi$ as the azimuth angle normal to the plane from the z-axis; and $\theta$ as the polar angle of rotation around the z-axis. Therefore, the combined intensity value, $I_{CBUS}(x, y, z)$, of the 3D ultrasound ($V_{CBUS}$) will be given by Eq. (1):

$$I_{CBUS}(x, y, z) = I_{AB}(\theta)\, \sin^2\phi + \overline{I_{AB}}\, \cos^2\phi \qquad (1)$$

where $\overline{I_{AB}}$ is the mean voxel intensity of both volumes, shown in Eq. (2):

$$\overline{I_{AB}} = \frac{1}{2}(I_A(x, y, z) + I_B(x, y, z)) \qquad (2)$$

and $I_{AB}(\theta)$ is the spherical-weighted sum of voxel intensities for each of the two intersecting orthogonal 2D ultrasound image planes, assuming that the in-plane resolution is higher than the out-of-plane resolution, as shown in Eq. (3):

$$I_{AB}(\theta) = I_A(x, y, z) \cos^2\theta + I_B(x, y, z) \sin^2\theta \qquad (3)$$

Therefore, viewing the 3D ultrasound image at any plane perpendicular to the z-axis, such as in the coronal view plane when $\phi=0$, 180, will display the average of the original 3DUS images [Eq. (2)]. Otherwise, any oblique C3DUS view plane for $180>\phi>0$, will result in the spherical-weighted sum of voxel intensities, $I_{CBUS}(x, y, z)$ [Eq. (1)].

Since the ultrasound beam has a thickness, the image data obtained at any 2D image plane will be an average of the intensity in the volume below the transducer. This means that although the 2D image plane is a representative image comprising pixels each with a pixel intensity on a 2D plane, the image is actually a volumetric representation of the volume under the transducer acquisition region represented by a set of volumetric elements or voxels. Preferably, the plane step interval, or distance between each 2D image acquired, is smaller than the volumetric thickness captured by each 2D scan, ensuring volumetric overlap between 2D image planes.

The plurality of 2D ultrasound image planes acquired from a transducer sweep of an ultrasound transducer first across a first scanning axis 22a, shown in volume $V_A$, and then again along a second scanning axis 22b angled, for example perpendicularly, to the first scanning axis, shown in volume $V_B$. As the first scanning axis 22a and second scanning axis 22b are orthogonal to one another, the 2D ultrasound image planes acquired along each orthogonal scanning axes 22a, 22b will also be orthogonal to one another. Further, the step interval between each of the 2D ultrasound image planes provides a normalized plane distance and therefore voxel size in the 3D ultrasound image.

While the acquired 3D ultrasound images have a high in-plane resolution, the out-of-plane resolution is poor due to the intrinsic elevational ultrasound resolution in the scanning direction. However, acquiring two sets of 3DUS images at an offset angle and then combining the two 3DUS datasets can provide an opportunity to visualize a display plane at any display angle through the ultrasound volume with improved image resolution uniformity by recovering out-of-plane resolution. In one preferable example the offset angle is 90°, and the scanning axes are orthogonal. Assuming that orthogonal 3DUS images occupy the same volume or have substantial overlap in physical space, the intensity values at any overlapped voxel coordinate in the display image on the display plane, I(x, y, z), can be combined with a spherical-weighted function of voxel intensities from the two original orthogonal 3DUS images, enhancing image resolution and improving out-of-plane resolution in 3DUS images. In this way, multi-modal image registration and reconstruction can be used for improving spatial resolution, in particular in out-of-plane regions and at oblique angles relative to the acquired 2D image planes.

Assuming that the orthogonal 3DUS images occupy the same volume or have substantial overlap in physical space, the intensity value of any pixel in the dataset at any overlapped voxel coordinate I(x,y,z) should be approximately the same. In combined 3DUS datasets, this provides an additional opportunity to normalize intensity values between the two orthogonal 3DUS scans by comparing one or more locations in the object volume where there is image acquisition overlap and adjusting the intensity of other pixels in the 3DUS data such that the intensity values of both 3DUS datasets are normalized.

To create the combined 3DUS and create a display plane at an oblique angle through the C3DUS acquisition volume, a spherical-weighted combination approach can be used for extrapolating pixel intensity at locations on the oblique display plane to generate a high-resolution ultrasound image in the desired display plane. The present method and system can thereby be used to capture and store the multiple 3D ultrasound images and any oblique plane through the volume can be sampled and configured for display on a graphical user interface. C3DUS as described improves resolution uniformity from in-plane to out-of-plane acquisition directions from complementary orthogonal 3DUS images and is a versatile method to improve 3DUS image resolution with the use of any conventional linear array ultrasound transducer.

Figure 6A:
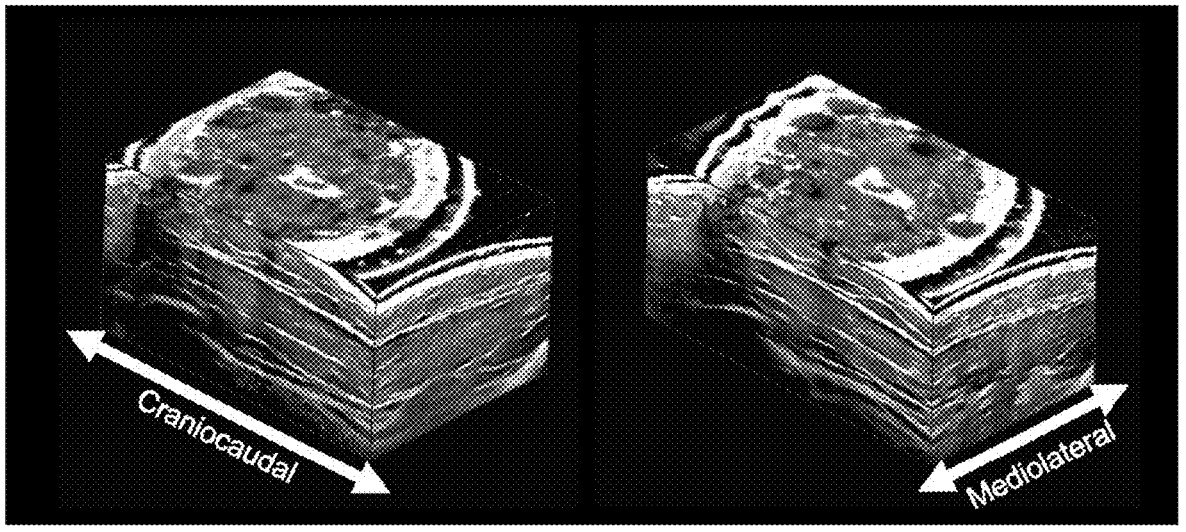
FIG. 6A is an orthogonal 3DUS image acquired in a healthy male volunteer along a first scanning axis in an ABUS scan.
Figure 6B:
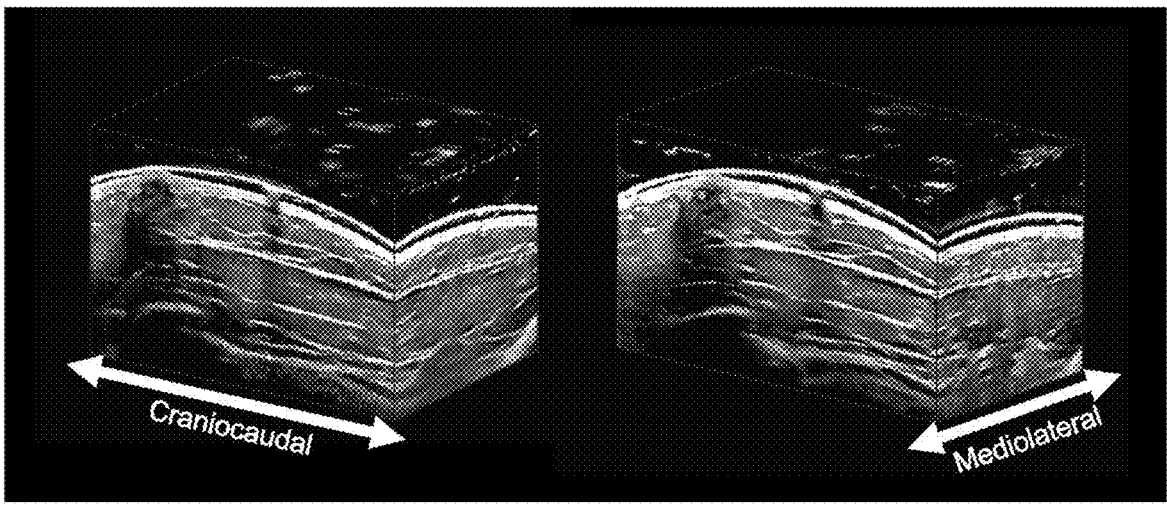
FIG. 6B is an orthogonal 3DUS image acquired in a healthy male volunteer along a second scanning axis in an ABUS scan.

FIGS. 6A and 6B are the two orthogonal 3DUS images acquired in a healthy male volunteer used to create the orthogonal plane images shown in FIG. 1. The arrows denote the acquisition (out-of-plane) direction of corresponding view planes in the breast. Orthogonal 3DUS acquisition and 3D breast ultrasound image acquisition was performed using a Canon® Aplio i800 ultrasound system (Canon Medical Systems, Tochigi, Japan) a high-resolution 14L5 (PLT-1005BT) (10 MHz) linear array ultrasound transducer with a 58 mm footprint width. Ultrasound penetration depth settings of 30-80 mm in 5.0 mm increments and 28-76 mm (28, 38, 47, 57, and 76 mm) were used for the Canon 14L5 and BK 8804 US transducers, respectively. 2D breast ultrasound scans were acquired using the dedicated ABUS device described herein, however it is understood that other devices may also be used for obtaining the plurality of orthogonal 2D ultrasound images used to create a 3D ultrasound image using the presently described method and system.

The dedicated 3D ABUS system is connected by Universal Serial Bus (USB) to a portable computer and monitor to interface with custom in-house workstation software with modules for image acquisition, 3D ultrasound image reconstruction and multiplanar visualization, multi-image registration and fusion of 3D ultrasound images, orthogonal 3D ultrasound combination, and 3D ultrasound visualization. An embedded or external imaging device control system can be used to control the translation mechanism in the ABUS 3D imaging device. To acquire 2D ultrasound images, the ultrasound transducer was translated along the first scanning axis a pre-set scan distance that is selected based on the dam size and ultrasound transducer dimension constraints. As the ultrasound transducer is translated across the scanning axis, 2D ultrasound images are acquired at a step interval along the first scanning axis to provide consistent spacing between pixels in the 2D ultrasound image, and ultimately between voxels in the 3D ultrasound image. The 2D ultrasound image collection was then repeated in a second scanning axis orthogonal to the first scanning axis to capture a full set of images for creating the 3D image of the breast. The location of the transducer relative to the patient's chest wall can be adjusted laterally to ensure sufficient imaging coverage of the entire breast.

The 2D ultrasound images were acquired directly from the ultrasound transducer connected to a computer and monitor with an Epiphan Digital Visual Interface (DVI) to Universal Serial Bus (USB) video frame grabber (Epiphan Systems, Inc., Ottawa, Ontario, Canada). Since the width of most conventional 2D linear array ultrasound transducers are unable to cover the entire breast volume during a single scan, an ultrasound cradle which connects the transducer to the translation mechanism can be shifted laterally by a known distance, referred to herein as the step interval, to acquire a plurality of 2D images. The 2D image acquisition parameters and scan volume dimensions such as, for example, scan distance, lateral translation, and depth settings, can also be manually adjusted. The resulting display image at the display plane, which is a 2D ultrasound image comprised of combined data from two 3DUS datasets at out of plane and/or oblique angles, can then be reconstructed in real-time after the completion of the set of 2D scans along two orthogonal scanning axes is captured. For each 2D ultrasound image plane two or more parallel and partially overlapping 3D US images can be combined using a rigid registration and a voxel-based algorithm to assign the intensity values of overlapping 3D voxels. The final fused image depicts a whole breast 3D ultrasound image volume that can be viewed using 3D multiplanar viewing software.

Figure 7A:
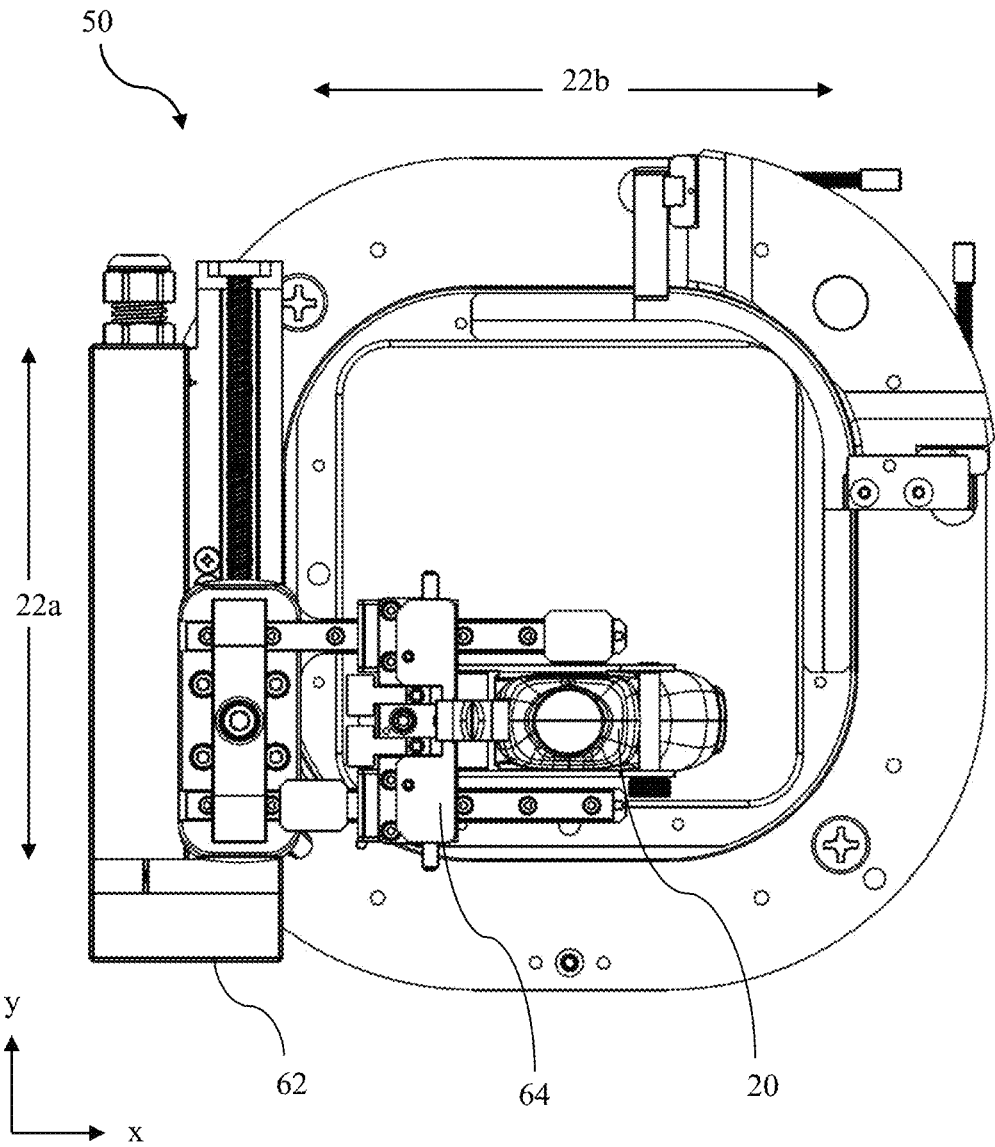
FIG. 7A is a top view of an example compact 3D automated breast ultrasound device illustrating the translation assembly and craniocaudal and mediolateral planes orientations.

FIG. 7A is a top view of an example compact 3D automated breast ultrasound (ABUS) imaging device illustrating the translation assembly 62 and craniocaudal plane and mediolateral plane orientations. The 3D ABUS imaging device 50 is designed to sit around a breast and support the acquisition of two orthogonal 3DUS image datasets. Transducer cradle 64 is designed to secure a standard handheld ultrasound transducer 20 such that the transducer can be controllably moved along a scanning axis 22a. In the design shown the translation assembly 62 can also be relocated to align with scanning axis 22b to capture a second set of 2D image planes orthogonal to a second scanning axis. Combining a 3D image capturing system such as the one shown for breast imaging with the present method and system for oblique plane visualization in 3D ultrasound provides for increased image size and/or resolution with low processing requirements in a portable system, removing the need for medical cart-based systems and mechanical arms for automated scanning may provide a cost-effective, portable and hands-free whole-breast 3D ultrasound imaging technique, including bedside point-of-care (POC). Compared with specialized 3D automated breast ultrasound systems, hybrid approaches can use conventional linear array ultrasound transducers which are cost-effective and widely available in clinical practice.

Figure 7B:
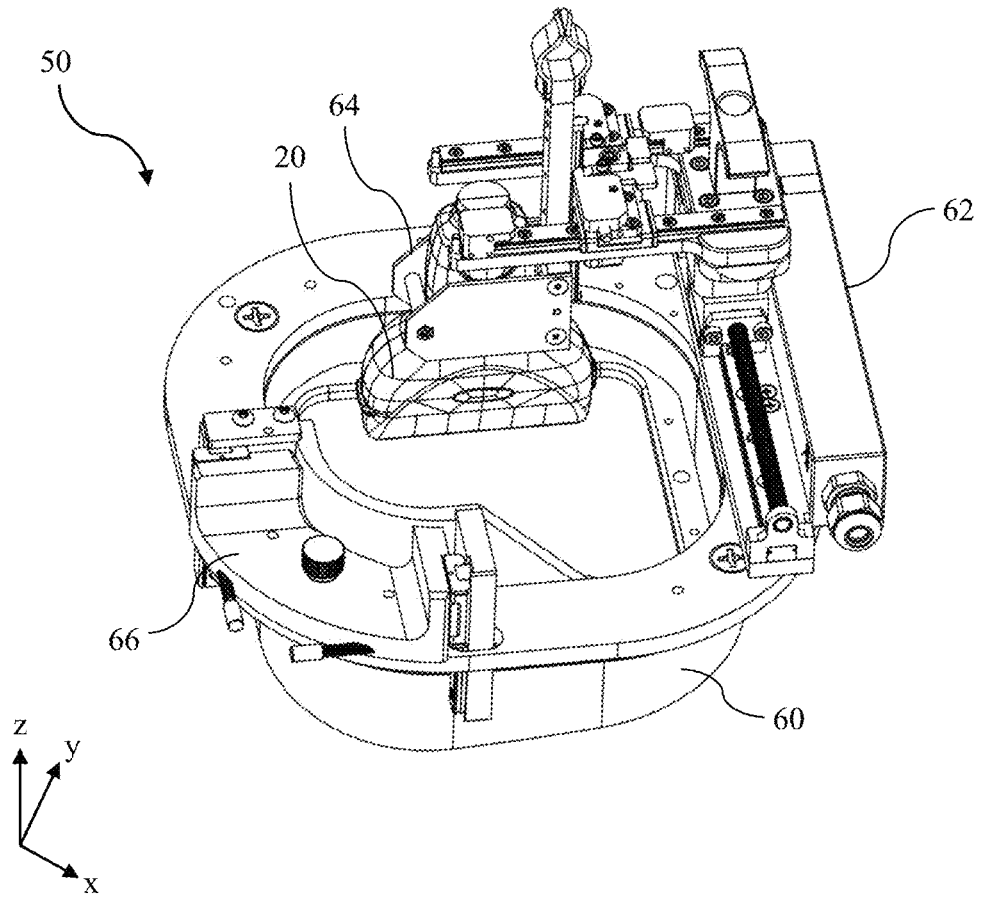
FIG. 7B is an isometric view of an example compact, dedicated 3D automated breast ultrasound device which can be used with the present method and system.

FIG. 7B is an isometric view of an example compact, dedicated 3D automated breast ultrasound (ABUS) device which can be used with the present method and system. The ABUS device shown is a wearable 3D imaging device 50 with a dam assembly 60, which is optionally 3D-printed, that comfortably conforms to the patient, an adjustable compression assembly 66 to stabilize anatomy or reduce tissue thickness without painful application, and a removable ultrasound scanner that fits into a transducer cradle 64, which is connected with a motorized-drive mechanism or translation assembly 62 to translate the transducer cradle 64 with the seated ultrasound transducer for automated 3D ultrasound image acquisition. The dam assembly 60 contains a removable top plate that serves as the base of the 3D ABUS system and supports the removable 3DUS scanner and optional compression plate assembly. The transducer cradle 64 is versatile and adaptable and designed to accommodate a wide variety of commercially available linear ultrasound transducers. The translation assembly 62 shown can be positioned in two configurations: in the craniocaudal direction plane to acquire transverse 2D ultrasound images; and in the mediolateral direction plane to acquire sagittal 2D ultrasound images. The translation assembly 62 can have a quick-release connection such that the transducer cradle 64 and its seated ultrasound transducer can be interchangeably positioned in either of the mediolateral or craniocaudal planar configurations. Optionally the quick release mechanism can comprise two or more stabilization magnets, optionally with locating pins.

Whole breast 3D ultrasound imaging systems are cost-effective, portable, and hands-free and can be used for bedside point-of-care imaging. Whole breast 3D ultrasound imaging systems are particularly useful for acquiring clear, sharp 3D ultrasound images of dense and/or small breasts. Further, whole breast 3D ultrasound imaging systems such as the one shown can provide a portable, lightweight device which can be used together with a conventional hand-held 3D ultrasound transducer or a motorized sweeping assembly. The portable 3D ultrasound imaging system is cost-effective, portable and hands-free and can be used for bedside point-of-care imaging to acquire clear, sharp 3D ultrasound images, and is particularly useful in the capture of ultrasound images of dense and/or small breasts which can be difficult to image using other method. In use of the shown imaging system a 2D ultrasound transducer moves with the subject while the subject is breathing resulting in clearer 3D ultrasound images, while facilitating scanning with the ultrasound transducer over a surface of a conventional ultrasound compression plate to obtain multiple 3D ultrasound images.

Figure 8:
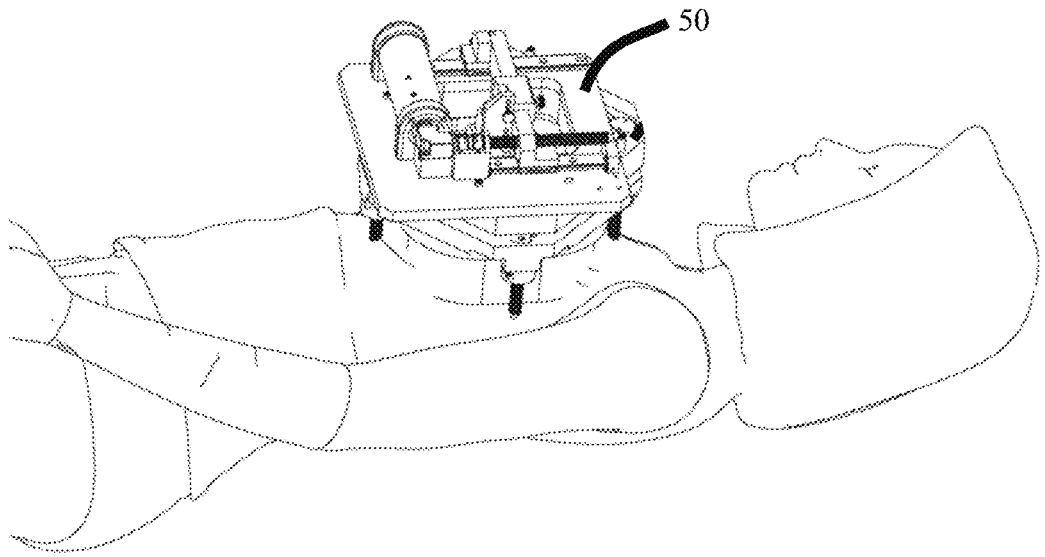
FIG. 8 depicts a subject with a 3D ultrasound imaging system mounted on their subject left breast for capturing a whole breast 3D ultrasound image.

FIG. 8 depicts a subject with a 3D ultrasound ABUS imaging system mounted on their left breast for capturing a whole breast 3D ultrasound image. In one application, a cost-effective, portable, dedicated 3D automated breast ultrasound device comprises a wearable 3D-printed dam assembly, an adjustable compression assembly, and a motorized translation assembly connected to a handheld ultrasound transducer for 3D ultrasound image acquisition which can accommodate any conventional linear array ultrasound transducer. The motorized translation assembly can be connected to and used to translate any commercially available linear array US transducer to collect a plurality of 2D ultrasound image planes which can be used to generate a 3D US ultrasound. The motorized translation assembly can be positioned on the dam assembly in, for example, craniocaudal and/or mediolateral orientations to acquire axial and sagittal 2D ultrasound images, respectively. The orthogonal 2D ultrasound images captured then can be reconstructed into a volumetric 3D ultrasound image.

Other methods of acquiring orthogonal 2D ultrasound image planes can be used with the present method and system. In one example a subject is supine lying face up and a mechanical arm holding an ultrasound transducer is deployed over the subject. The transducer is then swept across the surface of the breast. In another example called the "pendulous" approach, a subject lies prone face down over a cavity in an imaging table with the breast hanging into the cavity. The cavity is filled with ultrasound transmission fluid, for example ultrasound gel or water, and an ultrasound transducer is manipulated over the exterior of the cavity from underneath the table. In both cases orthogonal sets of 2D ultrasound image planes can be acquired by the transducer and converted into a 3D ultrasound image as presently described.

Figure 9:
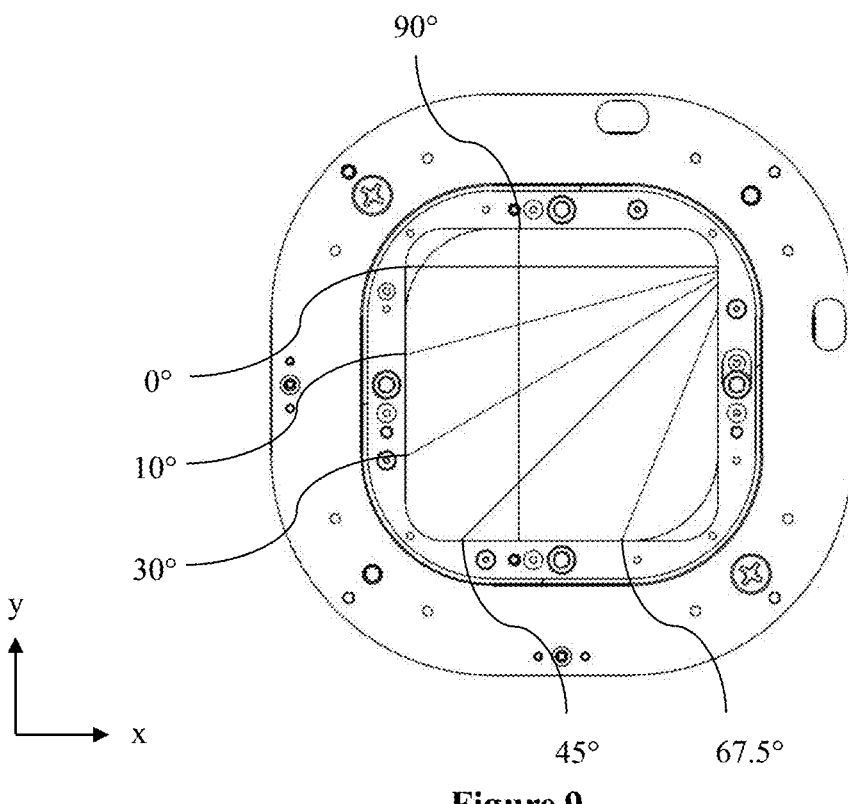
FIG. 9 is an illustration of a custom angular wire phantom used for experimental validation.

FIG. 9 is an illustration of a custom angular wire phantom used for experimental validation. Orthogonal 3DUS image acquisition and improvement in uniformity of image resolution in the combined 3DUS image were experimentally evaluated with a custom angular wire phantom as shown.

The angular wire phantom contains a configuration of six wires, made from 0.01-inch (0.254 mm) diameter monofilament thread, positioned at angles, 0°, 10°, 30°, 45°, 67.5°, and 90°, in the coronal plane. These wires were positioned in two layers spaced approximately 1.0-inch (2.54 cm) apart in the axial ultrasound direction, allowing for focal zone and far field resolution analysis at two different regions in the ultrasound beam. Sufficient distance was included between the wire layers to avoid artifacts from acoustic shadowing from the top layer for far zone analysis. The angular wire phantom was affixed to the 3D ABUS device on the dam assembly, allowing the removable scanner to be positioned in either the craniocaudal or mediolateral orientations for orthogonal 3DUS acquisition. A validation experiment was done to evaluate the orthogonal image acquisition and combination approach and assess its impact on spatial resolution volumes. Experimental validation was performed at various in-plane angles to evaluate the orthogonal 3DUS acquisition and spherical-weighted combination approach to generate a C3DUS image. The spatial resolution and its uniformity in the original orthogonal 3DUS and C3DUS images were then evaluated.

Figure 10:
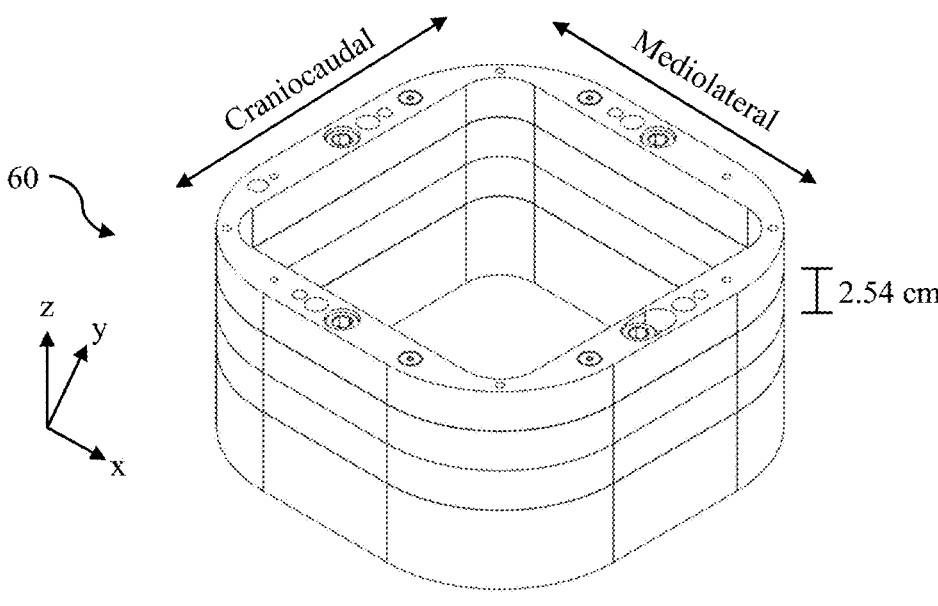
FIG. 10 is multi-layer apparatus that attaches onto a dam assembly of a 3D ultrasound acquisition device.

FIG. 10 is a multi-layer apparatus that attaches onto a dam assembly 60 of a 3D ultrasound image acquisition device. Each layer can connect with one or more wires spanning the layer, and 2.54 cm is shown as one example layer thickness. To evaluate the resolution in the orthogonal 3DUS and 3D CBUS images, the angular wire phantom assembly was submerged in a solution made from a mixture of distilled water and 7.25% isopropanol by volume at room temperature to mimic the speed-of-sound in human soft tissues of approximately 1540 m/s. A polyurethane-based film sheet was positioned under the angular wire phantom as an acoustic absorber to reduce artifacts due to reflection. To generate a 3D ABUS image, the scanner assembly was positioned on the phantom and the US transducer was lowered so that its front transducer face was slightly submerged in the solution. This experimental setup allowed for a uniform hypoechoic background to ensure the intensity spread of the wires in the angular phantom was clearly visualized for resolution analysis of the original orthogonal 3DUS and 3D CBUS images.

Figure 11:
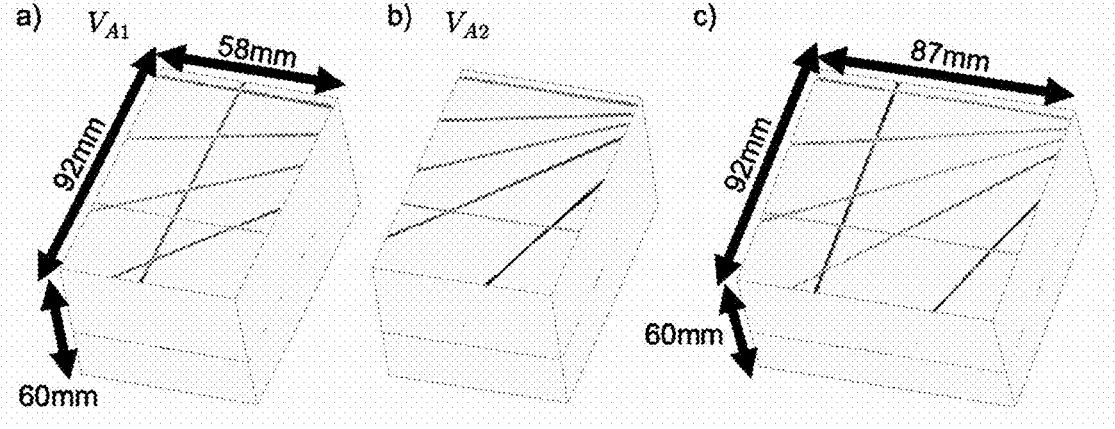
FIG. 11 is an illustration of two partially overlapping 3D ABUS images in the craniocaudal acquisition direction.

FIG. 11 is an illustration of two partially overlapping 3D ABUS images a) $V_{A1}$ and b) $V_{A2}$ with a 92 mm scan distance and 60 mm depth setting, and c) combined 3DUS image 92×87×60 mm$^3$ in volume, acquired with the Canon 14L5 US transducer in the craniocaudal acquisition direction. The original 3DUS images $V_A$ and $V_B$ and C3DUS image were analyzed to examine the effect of the orthogonal combination on image resolution. Using multiplanar reformatting, the 3DUS images were then viewed in the coronal plane such that the slice precisely bisected the angular wire phantom, as illustrated. To evaluate the spatial resolution, 2D images (N=2, each) were acquired and averaged by orthogonally slicing the central axis of each manually identified wire (0°, 10°, 30°, 45°, 67.5° and 90°) from the coronal view plane as shown in FIG. 9. Line profiles were acquired for each averaged 2DUS image slice in the lateral direction, which was expected to include both in-plane and out-of-plane components at any non-oblique angle.

Since 2D image extraction represents a slice of the acquired 3DUS image, the line profiles of the bisected wires depict the intensity pattern of the wires and are assumed to be equivalent to the line spread function (LSF) of each wire. The full width at half maximum (FWHM) measurements were made for the LSF of each wire. Since the spatial resolution of the 3DUS images is provided by the intensity spread of each wire, these FWHM measurements represent the 2D resolution measurement (axial and lateral directions) in the viewing plane of interest. For each wire, the lateral FWHM measurements were calculated. The mean and range (minimum to maximum) across the FWHM measurements for each 3DUS image ($V_A$, $V_B$ and $V_{C3DUS}$) were reported. The FWHM was plotted as a function of wire angle and linear regression analysis was performed to evaluate the relationship between the FWHM and wire angle for the original orthogonal 3DUS images.

Figure 12:
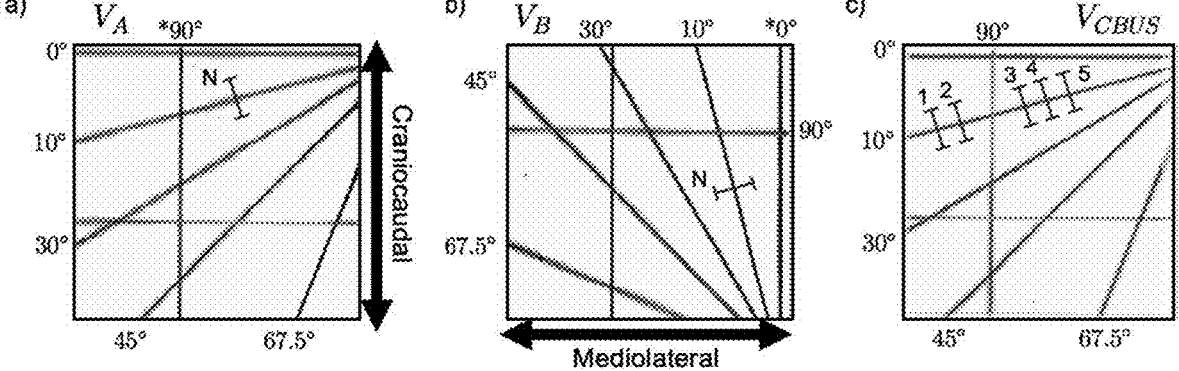
FIG. 12 is a set of coronal views of 3DUS images of the angular wire phantom in the craniocaudal ($V_A$), mediolateral ($V_B$), and, combined 3DUS image.

FIG. 12 is a set of coronal views of 3DUS images of the angular wire phantom in the craniocaudal ($V_A$), mediolateral ($V_B$), and combined 3DUS image. The coronal views are each taken at the bisection of the top layer of the angular wire phantom in the focal zone: a) craniocaudal ($V_A$) 3DUS image, b) mediolateral ($V_B$) 3DUS image, and c) combined 3DUS image. A directional arrow shows orthogonal 3DUS acquisition directions. The wire acquired in-plane with the acquisition direction, that coincides with the best resolution, is indicated with an asterisk on the original orthogonal 3DUS images. The overlaid numbered range bars in panel c) represent N orthogonal cross-section 2DUS slice for line profile and resolution analysis. The lowest in-plane resolution for $V_A$ occurs at 90° and $V_B$ occurs at 0°, which coincides with the best resolution as indicated for the craniocaudal and mediolateral directions. Linear regression analysis shows a strong correlation between FWHM and wire angle across the original volumes.

Figure 13:
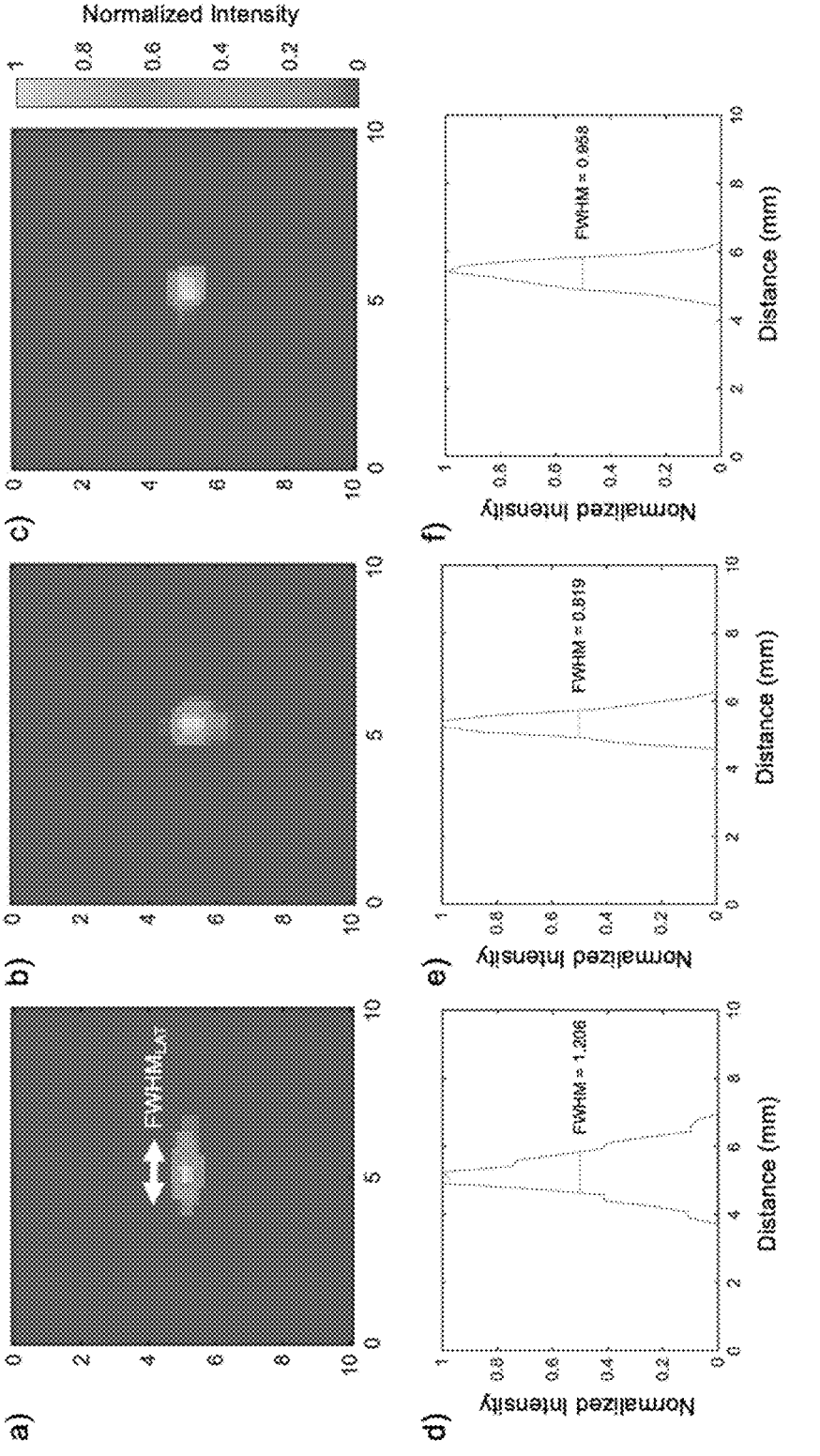
FIG. 13 illustrates averaged 2D US image slices for the craniocaudal ($V_A$), mediolateral ($V_B$), and combined 3DUS images.

FIG. 13 illustrates averaged 2D US image slices (N=2) from orthogonally slicing the central axis of the 10° manually segmented wire and lateral line spread profiles and full width at half maximum (FWHM) of a) craniocaudal ($V_A$), b) mediolateral ($V_B$), and c) CBUS image volumes. Orthogonal 3DUS images, $V_A$ and $V_B$, of the angular wire phantom were acquired with the 3D ABUS device using the Canon 14L5 ultrasound transducer. To evaluate the impact of poor elevational resolution and loss of resolution in the 3DUS scanning direction, the 2DUS frame density setting was varied from 2, 4, and 6 frames per mm, which were selected as undersampling to oversampling the acquisition of 2DUS frames. A penetration depth setting of 60 mm and 57 mm was selected for the Canon 14L5 ultrasound transducer, and the ultrasound focal zone was positioned at the bisection of the top layer of wires at approximately 2.0 cm in depth. To ensure all wires were visible in the 3DUS image, a scan distance of 92.0 mm in the craniocaudal and mediolateral directions, and lateral translation distance of 30.0 mm for acquisition of the second parallel image were used.

Orthogonal 3DUS images ($V_A$ and $V_B$) with dimensions of 92×87×60 mm (width×scan distance×depth) for each in-plane translation and rotation for combining the two orthogonal images were determined based on an initial calibration to align the cross-hairs of orthogonal wires (00 and 90°) using the first acquired 3DUS image dataset ($V_A$ and $V_B$). For each 3DUS image ($V_A$ and $V_B$), the image and voxel sizes for each frame density setting (2, 4, and 6 frames per mm) and acquisition times are shown in Table I, which shows 3DUS image volume, number of voxels, and voxel size for variable frame density parameters for orthogonal 3DUS and 3D combined 3DUS images obtained with a Canon 14L5 ultrasound transducer. Across these acquisition parameters, a single 3D ABUS image takes approximately 8-40 seconds to acquire depending on the frame density, as shown in Table I. A 2DUS image acquisition frame rate of 25 frames per second (FPS) was selected, consistent with the frame rate settings for high-resolution breast imaging applications. The 3D CBUS image volume for the Canon 14L5 ultrasound transducer with these acquisition parameters were 488×345×976 voxels with an isotropic voxel size of 0.174×0.174×0.174 mm³.

TABLE I

| 3DUS Image Volume Dimensions | | 92 × 87 × 60 mm |
| Frame Density: | | |
|---|---|---|
| 2 Frames mm⁻¹ | Number of Voxels | 488 × 345 × 92 voxels |
| | (Voxel Size) | (0.174 × 0.174 × 1.0 mm³) |
| | Acquisition Time | 8 sec (4 sec per scan) |
| 4 Frames mm⁻¹ | Number of Voxels | 488 × 345 × 184 voxels |
| | (Voxel Size) | (0.174 × 0.174 × 0.5 mm³) |
| | Acquisition Time | 16 sec (8 sec per scan) |
| 6 Frames mm⁻¹ | Number of Voxels | 488 × 345 × 276 voxels |
| | (Voxel Size) | (0.174 × 0.174 × 0.330 mm³) |
| | Acquisition Time | 28 sec (14 sec per scan) |
| C3DUS | Number of Voxels | 488 × 345 × 976 voxels |
| | (Voxel Size) | (0.174 × 0.174 × 0.174 mm³) |
| | Acquisition Time | 44 sec (22 sec per scan) |

The original 3DUS ($V_A$ and $V_B$) and C3DUS ($V_{3DUS}$) images were analyzed to examine the effect of the orthogonal combination on 3D resolution by determining the full width at half maximum (FWHM) for the angular wires across various 3D CBUS image cutting planes. All post-acquisition image analysis was performed using MATLAB R2022 (MathWorks, Natick, Massachusetts, United States) for a) craniocaudal ($V_A$), b) mediolateral ($V_B$), and c) combined 3DUS image volumes. The axial and lateral resolution, as the full width at half maximum (FWHM) in orthogonal cross-section views of the wires from the original orthogonal 3D ultrasound and 3D CB ultrasound images was determined.

To evaluate FWHM resolution (i.e., when $\phi=0$) as a function of angle, $\theta$, the 3DUS images were evaluated by extracting a 2D coronal image slices that were perpendicular (orthogonal cross-section) to each wire (0°, 10°, 30°, 45°, 67.5° and 90°), as shown in FIG. 13. Multiple 2D image slices at a plane step interval of 1.0 mm (10-2D image planes acquired in 10 mm, N=5, each) orthogonal to the central axis of each wire were extracted, allowing for averaging to obtain a better estimate of the FWHM. When 2D US image slices were extracted for FWHM resolution analysis, a calibration factor was applied to the B-mode greyscale intensity values, which were digitized from 0-255. This calibration factor was used to correct the greyscale intensity data that was output to the workstation to the values measured by the ultrasound transducer. Calibration factors were applied to the 3DUS images collected by each ultrasound transducer, which were determined using a CIRS Sono403 Multi-Purpose Phantom (Model 040GSE, Sun Nuclear, Norfolk, Virginia, United States).

Using the Canon 14L5 US transducer, the correction factor was determined to be described by Eq. (4):

$$I'[dB]_{CAN} = \frac{(I[dB] - 74)}{3.6} \quad (4)$$

The corrected intensity values were then normalized from 0-1 for FWHM analysis.

Line profiles of intensity values of the images, or intensity as a function of off-axis distance from the center axis of the wire, were obtained for each corrected 2DUS image slice in the lateral and axial directions. At any oblique angle (i.e., $\theta \neq 0$, 90) the lateral resolution measurement is expected to include both in-plane and out-of-plane components. With the lateral and axial line profiles of each wire, the FWHM measurements were obtained for each wire. The mean FWHM and standard deviation (SD) across multiple 2DUS images (N=5) was calculated for each 3DUS image ($V_A$, $V_B$ and $V_{3DUS}$) for Canon 14L5 and BK 8804 US transducers for each frame density (2, 4, and 6 frames per mm) parameter and US focal and far zones.

All statistical calculations and analysis were performed with MATLAB R2022 with a statistical significance level of 0.05, which corresponds to a 95% confidence. Shapiro-Wilk tests were performed to examine the normality of distributions of the FWHM data. Unpaired Student's t-tests were performed between the mean axial and lateral FWHM resolutions for each wire between the orthogonal 3DUS images ($V_A$ and $V_B$) and the 3D CBUS image ($V_{3DUS}$) to evaluate for statistical differences. These statistical tests were repeated to assess for significance for each variable frame density (2, 4, 6 frames per mm) and focal zones. The FWHM resolution was plotted as a function of wire angle. For the original orthogonal 3DUS images, linear regression analysis was performed to estimate the relationship between the FWHM measurements and wire angle. The coefficient of determination ($R^2$) was computed to evaluate the strength of relationship, where the strength of relationship between was determined as low (0.0-0.4), moderate (0.4-0.8) and high (0.8-1.0) correlation.

With the experimental 3D ABUS scan parameters, in-plane translational and rotational calibration values based on an initial calibration using a single acquired 3DUS image dataset ($V_A$ and $V_B$) with 4 frames per mm frame density parameters are summarized in Table II, which provides 3D CBUS calibration parameters with experimental 3D ABUS image acquisition parameters.

TABLE II

| | | Canon 14L5 US Transducer |
|---|---|---|
| Translation | x-axis | 24 pixels (4.18 mm) |
| | y-axis | 46 pixels (8.00 mm) |
| Rotation | | 90.0° |

The Canon 14L5 US transducer has a frame density of 2, 4, 6 frames per mm and a focal zone and far zone. The lateral and axial FWHM measurements across the angular wires showed mean and range values of 1.05 (0.68-1.39) mm, 1.07 (0.58-1.54) mm, and 0.90 (0.79-0.98) mm for $V_A$, $V_B$ and $V_{3DUS}$ image volumes, respectively. In comparison to FWHM measurements in the orthogonal 3DUS image volumes, the range in the C3DUS image volume was more constrained, which suggests that there is a reduced angular dependence from out-of-plane and in-plane resolution components in the C3DUS image. Specifically, the amount of blur or spread that is inherently present in the orthogonal images due to the out-of-plane component is overcome upon combination, as they contribute greater weightings in the combined 3DUS voxels.

One example of the averaged orthogonal 2D ultrasound image slices (N=2) as the pixel intensity maps for the 10° wire and lateral line spread profiles and FWHM measurements are shown for the craniocaudal ($V_A$), mediolateral ($V_B$), and $V_{CBUS}$ volumes. With this 10° wire, the C3DUS image volume recovered some out-of-plane resolution from the craniocaudal (predominantly out-of-plane) volume with the mediolateral (predominantly in-plane) volume. With this linear 3D ultrasound acquisition approach, the geometric 3DUS reconstruction accuracy was validated demonstrating excellent linear and volumetric reconstruction accuracy.

Figure 14:
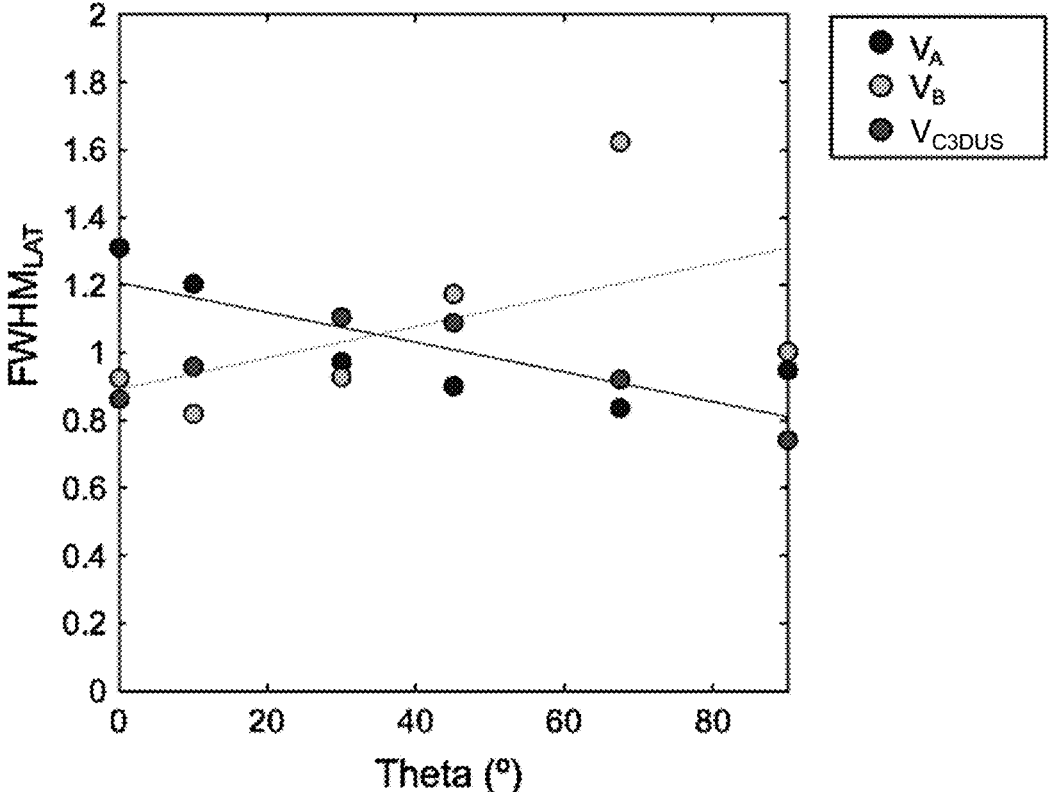
FIG. 14 is an graph of lateral full width half maximum FWHM as a function of wire angle in a phantom wire validation experiment.

FIG. 14 is a graph of lateral full width half maximum FWHM (FWHMLAT) as a function of wire angle. A comprehensive resolution analysis and comparison of the original orthogonal 3DUS images and C3DUS images was performed by comparing lateral FWHM (FWHM$_{LAT}$) as a function of wire angle for a) craniocaudal ($V_A$) mediolateral ($V_B$), and c) $V_{CBUS}$ combined breast image volumes. The in-plane wire, which coincides with the best resolution is indicated for the craniocaudal (CC) and mediolateral (ML) arrows. Linear regression analysis shows a strong correlation between FWHM and wire angle across all three volumes. The lateral and axial FWHM measurements were evaluated as a function of wire angle to assess the trends from in-plane to out-of-plane, with respect to acquisition direction, as shown in FIG. 12. In the craniocaudal 3DUS image volume, the FWHM shows a decreasing trend when moving from the 0° (out-of-plane) to 90° (in-plane) wire. In the mediolateral 3DUS image volume, the FWHM shows a complementary increasing trend when moving from the 0° (in-plane) to the 90° (out-of-plane) wire, as expected based on the scanning geometry. These FWHM trends are consistent with the image quality, as visualized as blurring of the angular wires, in the coronal view plane.

Linear regression analysis resulted in R$^2$ values of 0.80, 0.99, and 0.81 for the craniocaudal, mediolateral, and CBUS volumes respectively, which suggests a high level of correlation between FWHM and wire angle across all three volumes. It is evident that the resolution of the C3DUS image was improved with the voxel combination approach. Moreover, combined 3DUS removes the dependency of viewing the 3DUS image volume in-plane or out-of-plane, enabling a more reliable high-resolution 3DUS image. Since a 2DUS image extraction represents a slice of the 3DUS image, the line profiles depict the intensity pattern of the wires and are assumed equivalent to the line spread function (LSF) of each wire in the view plane of interest. This provides a validation of the C3DUS approach with orthogonal images acquired with a high-resolution US transducer (Canon 14L5) used for breast imaging applications, and a low-resolution US transducer (BK 8804), without the typical recommended resolution requirements for breast imaging.

The impact of 2DUS frame density on combined 3DUS image resolution was also evaluated. The results from this comprehensive analysis allow for insights into the potential efficiency of combined 3DUS for screening applications, which requires optimizing the acquisition parameters, while ensuring high-quality images are acquired for accurate whole breast diagnostic evaluation.

All publications, patents and patent applications mentioned in this specification are indicative of the level of skill of those skilled in the art to which this invention pertains and are herein incorporated by reference. The reference to any prior art in this specification is not, and should not be taken as, an acknowledgement or any form of suggestion that such prior art forms part of the common general knowledge.

The invention being thus described, it will be obvious that the same may be varied in many ways. Such variations are not to be regarded as a departure from the scope of the invention, and all such modifications as would be obvious to one skilled in the art are intended to be included within the scope of the following claims.

The invention claimed is:

1. A computer-implemented imaging method comprising: acquiring a first plurality of two-dimensional (2D) ultrasound images through an ultrasound volume, the first plurality of 2D ultrasound images normal to a first scanning axis, to provide a first three-dimensional ultrasound (3DUS) dataset;

acquiring a second plurality of 2D ultrasound images through the same ultrasound volume, the second plurality of 2D ultrasound images normal to a second scanning axis, the second scanning axis at an offset angle to the first scanning axis, to provide a second 3DUS dataset that is angularly offset relative to the first 3DUS dataset, the second 3DUS dataset overlapping the first 3DUS dataset;

selecting a display plane through the ultrasound volume, the display plane having a display angle relative to the first scanning axis and the second scanning axis;

constructing a display image sliced through the ultrasound volume on the display plane by calculating pixel intensity for a plurality of pixels at a location in the display image, the pixel intensity calculated using pixel weighting of pixels from the first 3DUS dataset in the location and from the second angularly offset 3DUS dataset in the same location, the calculated pixel intensity based on the display angle relative to the first scanning axis and the second scanning axis; and displaying the display image on a graphical user interface.

2. The method of claim 1, wherein constructing the display image at the display plane comprises using the same pixel weighting algorithm for calculating pixel intensity for all of the plurality of pixels in the image at the display plane.

3. The method of claim 1, wherein the offset angle is 90°.

4. The method of claim 1, wherein the ultrasound transducer has a minimum penetration depth of 30 millimeters (mm).

5. The method of claim 1, wherein pixel weighting for each of the plurality of pixels in the display image at the display plane comprises using a spherical-weighted algorithm.

6. The method of claim 1, further comprising normalizing pixel intensity values in the display plane by comparing pixel intensity at a coordinate location (x, y, z) in the first 3DUS and the second 3DUS and adjusting the pixel intensity in the display plane such that the pixel intensity for the first 3DUS dataset and the second 3DUS dataset are normalized.

7. The method of claim 1, wherein the first 3DUS dataset and the second 3DUS dataset are registered and fused using a rigid registration and voxel-based algorithm.

8. The method of claim 1, wherein the 2D ultrasound images contain intensity information from both in-plane and out-of-plane directions.

9. The method of claim 1, wherein the first plurality of 2D ultrasound images and second plurality of 2D ultrasound images are acquired with one or more of a linear transducer, a curvilinear transducer, a phased-array transducer, or a transducer that emits a single or multiple ultrasound wavelengths.

10. The method of claim 1, further comprising displaying a plurality of images at the same time, wherein each of the plurality of images is constructed at a different display plane through the ultrasound volume.

11. The method of claim 1, wherein each of the first scanning axis and the second scanning axis have a length of from 10 to 300 millimeters (mm).

12. The method of claim 1, wherein each of the 2D ultrasound images are acquired at a consistent step interval.

13. The method of claim 12, wherein the step interval is a spatial interval or a temporal interval.

14. The method of claim 12, wherein each acquired 2D ultrasound image has a volumetric plane width greater than the step interval.

15. The method of claim 12, wherein the step interval is a spatial interval and is from 1 to 10 frames per millimeter (mm).

16. An imaging system comprising:

an ultrasound transducer;

a three-dimensional (3D) imaging device comprising a translation mechanism that positions and translates the ultrasound transducer along a first scanning axis and a second scanning axis to collect a first three-dimensional ultrasound (3DUS) dataset normal to the first scanning axis and a second 3DUS dataset normal to the second scanning axis, the second 3DUS dataset being angularly offset relative to the first 3DUS dataset;

an imaging device control system that controls translation of the transducer;

an image processor that:

selects a display plane through an ultrasound volume, the display having a display angle relative to the first scanning axis and the second scanning axis; and, constructs a display image sliced through the ultrasound volume on a display plane by calculating pixel intensity for a plurality of pixels at a location in the display image, the pixel intensity calculated using pixel weighting of pixels from the first 3DUS dataset in the location and the second angularly offset 3DUS dataset in the same location, the calculated pixel intensity based on the display angle relative to the first scanning axis and the second scanning axis; and a graphical user interface for displaying the display image.

17. The system of claim 16, wherein the ultrasound transducer is a handheld ultrasound transducer connected to the translation mechanism.

18. The system of claim 16, wherein the image processor registers the first 3DUS dataset and the second 3DUS dataset using a rigid registration and voxel-based algorithm.

19. The system of claim 16, wherein transducer location information is provided from the imaging device control system to the image processor and used in registering the first 3DUS dataset and the second 3DUS dataset.

20. The system of claim 16, wherein the ultrasound transducer is one of a linear transducer, a curvilinear transducer, a phased-array transducer, or a transducer that emits a single or multiple ultrasound wavelengths.

* * * * *